(12) United States Patent
Rodriguez Quintero

(10) Patent No.: US 10,595,536 B2
(45) Date of Patent: *Mar. 24, 2020

(54) BIO-DERIVED COMPOSITIONS

(71) Applicant: Jose Alejandro Rodriguez Quintero, Valle del Cauca (CO)

(72) Inventor: Jose Alejandro Rodriguez Quintero, Valle del Cauca (CO)

(73) Assignee: Ibex Bionomics LLC, Coral Gables, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/177,199

(22) Filed: Feb. 10, 2014

(65) Prior Publication Data

US 2015/0223469 A1 Aug. 13, 2015

(51) Int. Cl.
*A01N 63/00* (2006.01)
*A01N 63/02* (2006.01)

(52) U.S. Cl.
CPC .................................. *A01N 63/02* (2013.01)

(58) Field of Classification Search
CPC .... A01N 63/04; A01N 2300/00; A01N 63/00; A01N 25/00; A01N 59/00; A01N 63/02; A01N 65/00; C02F 2209/02; C02F 2209/06; C02F 2209/08; C02F 2303/02; C02F 2307/00; C02F 1/72; C02F 2103/001; C02F 2103/005; C02F 2103/007; C02F 3/341; C02F 2209/005; C02F 3/006; C02F 3/34; C02F 1/5263; C02F 3/347; C02F 3/348; C12N 1/16; C12N 1/20; C12N 1/14; C12R 1/865; C12R 1/125
USPC ........ 210/601, 620; 424/725, 755, 776, 780; 435/252.1, 252.5, 255.2
IPC ............. A01N 63/00,65/00, 63/02; C02F 3/34, 3/00, 3/02; C11D 3/38; C12N 1/16, 1/20; A61K 36/31; A01G 1/00
See application file for complete search history.

(56) References Cited

U.S. PATENT DOCUMENTS

| 7,906,131 B2 * | 3/2011 | Brower | 424/405 |
| 2007/0172492 A1 * | 7/2007 | Soma et al. | 424/195.17 |
| 2010/0272701 A1 * | 10/2010 | Chen | 424/93.462 |
| 2010/0316763 A1 * | 12/2010 | Choi | A23L 3/3463 426/18 |
| 2014/0364309 A1 * | 12/2014 | Hellwege | A01N 43/40 504/100 |

FOREIGN PATENT DOCUMENTS

WO WO 2010109436 A1 * 9/2010 ............. C12N 11/00

OTHER PUBLICATIONS

Tang et al., 2004. Medium optimization or the production thermal stable β-glucanase by Bacillus subtilis ZJF-1A5 using response surface methodology, Bioresource Technology, vol. 93:175-181.*
Gibreel et al., 2009. Fermentation of Barley by Using *Saccharomyces cerevisiae*: Examinationof Barley as a Feedstock for Bioethanol Production and Value-Added Products. Applied and Environmental Microbiology, vol. 75(5):1363-1372.*
Renault et al., 2007. Characterization of Bacillus and Pseudomonas strains with suppressive traits isolated from tomato hydroponic-slow filtration unit. Canadian Journal of Microbiology, vol. 53, pp. 784-797.*
Manzoor, 2010. Bioinformatics assembly and analysis and annotation of the Bacillus amyloliquefaciens strain 5036 genome. Master's Thesis, Swedish University of Agricultural Sciences, Uppsala, 41 Pages.*
Leifert et al (1995. Antibiotic production and biocontrol activity by Bacillus subtilis CL27 and Bacillus pumilus CL45. Journal of Applied Bacteriology 1995, 70, 97-108.*
Federal Register2014-29414, 16 Pages.*
Jul. 30, 2015 Federal Register 18628 complete 37 Pages, p. 2, Appendices I-III.*
Singh et al .1984. Bacillus Subtiljs as a Control Agent Against Fungal Pathogens of Citrus Fruit. Transactions of the British Mycological Society, vol. 83 (3), pp. 487-490.*
Chen & Echandi .1984. Effects of avirulent bacteriocin-producing strains of Pseudomonas solanacearum on the control of bacterial wilt of tobacco. Plant Pathology, vol. 33, pp. 245-253.*
McLaughlin et al. 1988. Effects of avirulent bacteriocin-producing strains of Pseudomonas solanacearum on the control of bacterial wilt of tobacco. American Potato Journal, vol. 65, pp. 255-267.*
2008, New World Encyclopedia, http://www.newworldencyclopedia.org/p/index.php?title=Fermentation&oldid=679596 (Year: 2008).*
Kirk 2009. Bacillus subtilis. Microbe of the Week 2009.djwesten@mst.edu Bacillus subtilis p. 3 of 3 https://web.mst.edu/~microbio/BIO221_2009/B_subtilis.html, Printed Dec. 28, 2017. (Year: 2009).*
Romano, et al. 2005. Pseudomonas-*Saccharomyces* Interactions: Influence of Fungal Metabolism on Bacterial Physiology and Survival Journal of Bacteriology, vol. 187, pp. 940-948. (Year: 2005).*
Pal K. K. et al., "Biological control of plant pathogens", The Plant Health Instructor, 2006, DOI: 10.1094/PHI-A-2006-1117-02, pp. 1-25 . (Year: 2006).*

(Continued)

*Primary Examiner* — Satyendra K Singh
(74) *Attorney, Agent, or Firm* — Isaac Angres

(57) ABSTRACT

Described is a composition, which is a natural and organic pesticide, specifically for mitigating, controlling and treating fungicidal, virucidal and bactericidal pathogenic microorganisms in agricultural products such as root crops, fruits and vegetables. Examples of such disease-causing microorganisms are *Mycosphaerella fijensis* causing black Sigatoka disease in Cavendish (banana), *Ralstonia solanacearum* causing Moko disease in Cavendish (banana), *Lasiodiplodia theobromae* causing soft rot or fruit rot in crops and fruits, *Fusarium oxysporum* causing Panama wilt in fruits and crops, and many others. The composition is a fermented product of tropical plants, carbon source, protein (nitrogen) source, and a carrier agent. The fermented product may help strengthen the plant's immune system to fight pathogenic diseases. Since all the major constituents of the composition are generally regarded as safe, this natural pesticide is found to be non-toxic and safe to humans and animals, and environmentally benign.

6 Claims, 7 Drawing Sheets

(56) References Cited

OTHER PUBLICATIONS

Zoltan A. et al., Environmental Health Criteria 231—a WHO report 2005 entitled "Bentonite, Kaolin, and Selected Clay Minerals", printed pp. 1-196. (Year: 2005).*
CN 102002470 A—Derwent abstract Acc-No. 2011-F17533, attached pp. 1-2 (Year: 2011).*

* cited by examiner

BIO-DERIVED COMPOSITIONS

FIELD OF THE INVENTION

This invention relates to compositions and method for controlling plant diseases. More particularly, the invention relates to a composition prepared via microbiological fermentation and a method of use thereof for application to crop plants and soils for controlling plant diseases caused by pathogenic microorganisms.

This invention also relates generally to the field of compositions and methods for controlling of pests and pest populations which are known to be having a detrimental effect on human life and human activities. The invention also focuses on the isolation of these biopesticide compositions and formulations that are known to possess pesticidal properties and are derived from natural sources having biological origin which have been fermented with microorganisms. The invention more particularly describes the isolation and characterization, including but not confined to, novel biopesticide compositions possessing pesticidal attributes along with other pharmaceutically important attributes so as to also function as effective biocontrol agents.

The instant invention also relates to bio-pesticidal compositions or agents which exhibit excellent effects and in which there is no risk of pollution being caused thereby; and to a method for the use thereof. More particularly, the present invention relates to bio-pesticidal compositions for agricultural and horticultural use which comprise or consist of fermented products and a carrier for agricultural and horticultural formulation.

The present invention also concerns a novel method to treat, prevent and protect plants and agricultural plants from pathogenic attack and pest attacks. The present invention more particularly concerns a method of applying selected fermented products and compositions to a agricultural crops and its locus to treat, prevent and immunize, vis. induce local and systemic resistance of the crop against pesticidal and fungal diseases, wherein such action is referred to in this application as "induced plant defense". Such fermented compositions are applied directly to the plant or soil treat or prevent pesticidal diseases in plants and enhance its own immunization capacity via altering their metabolism.

This invention also pertains to products to treat rice diseases such as sheath blight, bacterial panicle blight, the tarsonemid mite and other diseases.

The invention also relates to fungicidal compositions and their applications in agriculture, and more particularly to fungicidal compositions that are particularly effective for the prevention of fungal damage and for the treatment of fungal diseases in plants and plant propagation material.

BACKGROUND OF THE INVENTION

Farming is the oldest wealth-creating business known to man. Current scientific strategies to maintain and improve yields in support of high-input agriculture place great emphasis on 'fail-safe' techniques for each component of the production sequence with little consideration of the integration of these components in a holistic, systems approach. Research for sustainable agricultural practices requires a far greater emphasis on such an approach than now is fashionable, despite all the rhetoric given politically to sustainability.

The populations of the world's poorest countries have been growing rapidly, increasing the demand for food. At the same time environmental degradation—both natural and man made—has reduced the ability of farmers to grow food in many areas. A lot has been written about the significant contribution due to "Green Revolution" and correctly so, especially considering our failure to control unsustainable population growth. Hardly any one argues that modern agriculture is sustainable. Besides, high input agriculture is increasingly recognized as an environment degrading and not profitable. We now recognize that technical progress may have social and environmental costs we cannot pay. People are now seriously concerned with the protection of the environment and even more about safeguarding their health. As now people realize that by consuming the standard agriculture based food products they are constantly taking in small quantities of poison of various kinds and much of this comes from the chemical pesticides that are used to produce food crops.

Modern farming requires large inputs of chemical fertilizer and stimulants to increase yields from hybrids. However for poor rural marginal farmers the use of chemical fertilizers and pesticides have made agriculture very expensive and to maintain yields in deteriorating soils increasing doses of modern chemical inputs have had to be used. The time has now come to consider alternative means of sustaining our agriculture and to protect the farmer from low prices, high indebtedness and to ensure that production incentives remain. For small farmers, organic farming is most suitable as considerable vertical integration is possible and appreciable cost savings could be achieved through the recycling of waste and other materials that are available within the system.

A considerable amount of literature is available on the practice of organic farming. Where organic farming is practiced, the farmer will use natural processes to enhance productivity, maintain the nutritive status of the soil to be less dependent on external resources and to keep his costs down. This will strengthen his social and financial position in the society. Organic farming uses natural materials which are the by products of the farm and are environmentally safe, it enhances the nutritive qualities of the soil and it nurtures the organisms in the soils, which are generally destroyed by the use of chemical manures and pesticides, and significantly reduces cost. Therefore, at this juncture further work on the development of agricultural biotechnology products based on natural products offers immense potential as viable alternative for sustainable agriculture.

Plants have remained central to every civilization as the primary source of life, due to their numerous applications in daily life. Plants are composed of chemical substances of which some are not directly beneficial for the growth and development of the organism. These secondary compounds have usually been regarded as a part of the plants' defense against plant-feeding insects and other herbivores. The pesticidal properties of many plants have been known for a long time and natural pesticides based on plant extracts such as rotenone, nicotine and pyrethrum have been commonly used in pest control.

Disease caused by various microorganisms such as fungi, bacteria, and viruses not only damage the plant as a whole but also severely affect quality of the crop. A number of physiological and biochemical alterations in the plants have been reported due to infection by fungi, bacteria, and viruses.

Improving soil fertility is one of the most common tactics to increase agricultural and forest production. Soil organisms, especially bacteria have a key role in determining the rate of organic matter decomposition and thereby nutrient mineralization. These processes determine the rate of nutrient supply to primary producers, largely determining the rate of biomass production and other fundamental ecosystem processes like interactions among different functional groups of organisms that constitute ecosystems. Therefore, elucidation of the mechanisms that determine species composition in plant communities is important. *Rhizobacteria*, once considered passive bystanders of the root environment, are now known to affect plant health, development, and environmental adaptation, both beneficially and detrimentally, and the importance of these bacteria in agriculture is expected to grow. A variety of mechanisms have been identified as being responsible for such plant growth promoting activity. For example, certain microorganisms indirectly promote plant growth by inhibiting the growth of deleterious microorganisms; or directly enhance plant growth by producing growth hormones; and/or by assisting in the uptake of nutrients by the crops, e.g., phosphorus.

Over the years, the demand for agricultural fruits, vegetables, and crops such as banana, mango, sweetpotato, cassava, and yam in the world market increased due to rising population and the influx of more novel applications in the food industry. Meanwhile, environment-friendly sustainable agricultural practices are getting more attractive to farmers since they have more benefits in doing such than the usual chemical control. The use of chemical agents for pests and diseases is disadvantageous because of high power consumption, soil and environment pollution, and the presence of pesticide residues, which are usually harsh chemicals, in fruits, vegetables, and crops harmful to humans and animals. The discovery of natural products that are beneficial to agriculture is highly important in addressing the concerns of farmers such as in increasing fruit, vegetable, and root crop yield and productivity.

Plant pests are a major factor in the loss of the world's commercially important agricultural crops resulting both in economic hardship to farmers and nutritional deprivation for local populations in many parts of the world. Broad spectrum chemical pesticides have been used extensively to control or eradicate pests of agricultural importance. There is, however, substantial interest in developing effective alternative pesticides.

Control of various pests through the use of biological molecules has been possible in only a limited number of cases. The best known examples of biological molecules with pesticidal uses are the δ-endotoxins from *Bacillus thuringiensis* (Bt), which is a gram-positive spore forming microorganism. Varieties of Bt are known that produce more than 25 different but related δ-endotoxins. Bt strains produce δ-endotoxins during sporulation the use of which is limited because they are active against only a very few of the many insect pests.

The limited specificity of the Bt endotoxins is dependent, at least in part, on both the activation of the toxin in the insect gut and its ability to bind to specific receptors present on the insects midgut epithelial cells. Therefore, the ability to control a specific insect pest using δ-endotoxins at present depends on the ability to find an appropriate δ-endotoxin with the desired range of activity. In many cases, no such δ-endotoxin is known, and it is not certain that one even exists.

Plants also routinely become infected by viruses, fungi and bacteria, and many microbial species have evolved to utilize the different niches provided by the growing plant. In addition to infection by fungi and bacteria, many plant diseases are caused by nematodes which are soil-borne and infect roots, typically causing serious damage when the same crop species is cultivated for successive years on the same area of ground.

The severity of the destructive process of disease depends on the aggressiveness of the phytopathogen and the response of the host, and one aim of most plant breeding programs is to increase the resistance of host plants to disease. Novel gene sources and combinations developed for resistance to disease have typically only had a limited period of successful use in many crop-pathogen systems due to the rapid evolution of phytopathogens to overcome resistance genes.

It is apparent, therefore, that scientists must constantly be in search of new methods with which to protect crops against plant pests. It has been found in the present invention a novel class of fermented products which can be used to control plant pests.

Programmed cell death is a process whereby developmental or environmental stimuli activate a genetic program that culminate in the death of the cell. This genetic potential exists in most, if not all, multicellular organisms. In the case of invertebrates, programmed cell death appears to play a dual role by being an integral part of both the insect development process and a response mechanism to infections particularly of viral nature. Programmed cell death appears to be executed in several different manners leading to either apoptosis, atrophy or differentiation. Apoptosis is one of the best characterized types of programmed cell death encompassing cytological changes including membrane-bound apoptotic bodies and cytoplasmic blebbing as well as molecular changes such as endonucleolysis typified by the generation of oligosomal length fragments. Although the overall apoptotic phenomenology is rather conserved among the different organisms, it is interesting to point out that, for many insect cells, cytoplasmic vacuolization and swelling rather than condensation seem to be the cytological features associated with apoptotic processes. The novel class of products disclosed within the present invention may also induce programmed cell death and exert a pesticidal effect.

Additionally, since crop yield decreases by as much as 30% to 100% in case of cultivating crops without pesticides, it is essential to use the pesticides for improving crop yield. However, improper use of synthetic chemical pesticides in crop production causes several problems such as nonselective toxicity, accumulation of toxic compounds and outbreak of pathogens resistant to the pesticides. One way to handle these problems is to develop biopesticides using fermented products incorporating certain microorganisms. Biopesticides are roughly classified into plant extracts, microorganisms, natural enemies, natural bioactive substances, fermentation products of certain plant materials and genetically modified organisms (GMO). Bio-pesticides can be safer, more biodegradable, and less expensive to develop than synthetic chemical pesticides.

The study on the development of biopesticides, especially microbial fungicides, has been a major interest in the field of plant pathology, and there is active interest in development of more effective products for different crops.

Plants are exposed to many microbes, including bacteria, viruses, fungi, and nematodes. Although many of the interactions between these microbes and plants are beneficial or innocuous, many of the interactions are harmful to the plants. Diseases of agricultural crops, ornamental plants, forests, and other plants caused by such plant pathogens, particularly bacterial pathogens, are a worldwide problem with enormous economic impact.

There are many pathogenic species of bacteria, fungi, and nematodes. Diseases caused by fungal species include preand post-emergence seedling damping off, hypocotyl rots, root rots, crown rots, and the like. Pathogenic nematodes cause diseases such as root galls, root rot, stunting, and various other rots. Some nematodes also function as vectors of plant viruses.

Bacterial pathogens have a significant impact on worldwide agriculture. Such plant pathogenic bacteria include species of *Pseudomonas, Erwinia, Agrobacterium, Xanthomonas,* and *Clavibacter. Pseudomonas* and *Xanthomonas* species affect a large number of different crops. For example, *Pseudomonas syringae* causes bacterial speck of tomato; *Xanthomonas campestris* pv. *malvacearum* causes angular leaf spot of cotton; *Pseudomonas solanacearum* causes bacterial wilt of potato; and *Pseudomonas tolaasii* causes brown blotch disease of cultivated mushrooms. Potatoes and many other crops, such as celery, head lettuce, carrot, Japanese radish, wasabi, tobacco, tomato, cyclamen, Chinese cabbage, and cabbage, are susceptible to the so-called bacterial soft rots.

*Erwinia carotovora* is a soft rot bacterium that softens and rots storage tissues of many plants and is reported to be ubiquitous in soil. The bacterium typically enters plant tissues through injuries caused by insects, wind, tools, and the like. The bacterium invades the site of injury, and if temperature and moisture conditions are suitable, the bacteria rapidly multiply and macerate the tissue. For example, *Erwinia* bacteria are latent in potato plants, and will preferentially attack the stem and the tubers only after wounding. Potato seed pieces are also susceptible to infection through the cut surfaces. *Erwinia carotovora* has a substantial impact on the potato industry.

Agricultural production of major crops has always been impeded by plant pathogens. Diseases caused by plant pathogens often limit the growth of certain crops to certain geographic locations and can destroy entire crops. Crop losses resulting from the deleterious effects of plant pathogens are, thus, a serious worldwide agricultural problem, particularly since there are no known treatments for many of the diseases caused by plant pathogens. Even in instances where agrichemicals and pesticides are effective against plant pathogens, their use is increasingly under attack because of injurious effects on the environment and human health.

Because pesticides are often ineffective, unavailable, and/or environmentally unacceptable, there is a need to develop alternative means for effectively eradicating or reducing the harmful effects of plant pathogens. In recent years, much research has focused on the development of means for biocontrol of such pathogens and on the development of pathogen-resistant plants by breeding or by genetic engineering. There are few examples, however, of successful production of effective biocontrol methods or disease-resistant plants.

Application of antibiotics, such as streptomycin, and metal compounds, such as copper-containing Bordeaux mixture, has been the conventional method of control for many bacterial diseases. For example, *Pseudomonas syringae* pv. tomato, which causes bacterial speck of tomato, is presently controlled by frequent application of copper-containing sprays, which, in addition to their unfavorable environmental impact, select for copper-resistant strains. Treatment of apple and pear orchards with streptomycin to control the fireblight pathogen, *Erwinia amylovora*, has resulted in the appearance of streptomycin-resistant strains. *Xanthomonas campestris* pv. *malvacearum*, which causes angular leaf spot of cotton, presently is controlled by treating seeds with mercury-containing compounds and copper sprays. Other *Xanthomonas campestris* species, such as *X. campestris* pv. *vesicatoria* and *X. campestris* pv. *campestris*, can be seed-borne, and there are no effective means for treating the seeds without injury thereto. These chemicals give unsatisfactory control, however, and also kill useful bacteria, contaminate the environment, and cause chemical injuries. Antibiotic-resistant bacteria have also appeared, and the ability of bacteria to transfer multiple drug resistance genes between genera potentially threatens antibiotic treatment of diseases of humans and/or animals.

Since there are few means for controlling plant bacterial pathogens, and those that are available, such as the heavy metal-containing sprays and antibiotics, are not highly effective and are environmentally unacceptable, and since there are relatively few bacterial pathogen-resistant vegetable or fruit plants available, there is a need for the development of effective, non-toxic, biodegradable and environmentally acceptable means for the control of plant pathogens. There is also a need to develop means for treating plants to eradicate or control plant diseases of numerous origins.

Additionally, the biological treatment or bioremediation of waste water, soil, oil spills, refinery waste, refinery and waste water treatment sludge contaminated with hydrocarbonaceous contaminants, and the like, is desirable. These processes depend on natural bacteria or fungi to biodegrade the typically hydrocarbon hydrocarbonaceous contaminants, into more environmentally friendly materials (bioremediation) and include, in addition to the well known aerobic and/or anaerobic processes for waste water treatment, processes used for the treatment of oil spills on water, land and the other contaminated substrates mentioned above. Cellulosic and lignin containing materials, along with bacteria and, if needed, nitrogen and phosphorous bacteria nutrients, are often used in the bioremediation of soil and other particulate solid or semi-solid substrates, such as sludges. Oil spills, especially on water, are particularly troublesome to treat, as are oil producing well sites contaminated with crude oil. Waste water processes, in addition to producing bioremediated wastewater, also produce contaminated sludge. This sludge must also be treated, to biodegrade the hydrocarbonaceous contaminants remaining in it. One or more cellulosic materials, such as wood chips and straw, are typically added to the sludge, as what is referred to as an amendment material, and mixed therewith to provide porosity and sites for the bioactive bacteria When treating land contaminated with hydrocarbonaceous material, such materials are mixed in with the land or soil, to form a composted mass in which the hydrocarbons biodegrade into carbon dioxide and water.

There is also a strong environmental and economic demand for accelerated activity bacteria capable of breaking down unwanted solids suspended or partially dissolved in aqueous media. Such solids have been classified in several ways including: total suspended solids (TSS), total volatile solids (TVS), sludge, and collectively, fats, oils and greases (FOG). Such solids have also been classified in their ability to enhance the life-bearing capabilities of the liquid in which they are suspended. Normal classifications include chemical oxygen demand (COD) and biological oxygen demand (BOD). Accelerated activity bacteria (i.e. highly active bacteria) have also been used to breakdown certain toxic wastes such as phenolic compounds and chromium by-products.

In a typical application, active bacteria, after acclimation, are used to treat toxic wastes to produce harmless, easily disposed non-toxic end products. Highly active bacteria have also been used to control or eliminate malodorous aqueous effluents. Malodorous substances such as hydrogen sulfide, ammonia or butyric acid, if broken down or denatured, are essentially odorless. An example of a material which falls in both the classifications of toxic material and malodorous material is hydrogen sulfide which, in its gaseous form or an aqueous solution is both toxic and malodorous.

Several strains of bacteria, normally found in soil, have been found to significantly shorten the breakdown cycle of solid wastes generally found in sewage. Examples of such soil bacteria include the genera of *Arthrobacter, Bacillus, Pseudomonas, Flavobacterium* and *Acinetobacter*, to mention a few. Certain bacteria found in animal intestines have been found to produce enzymes which, in turn, preferrably breakdown fats, oils and greases. Examples of such enzymes are found in many ruminant animals. Especially of note are the lipase producers found in sheep. Lastly, bacteria including varieties of *Rhodospirillum* and *Chromatium* are commonly found in salt water and have been found to rapidly and efficiently breakdown aqueous solutions of hydrogen sulfide. These are but a few examples of the many circumstances in which bacteria found in one environment can be usefully employed to remove unwanted species and solutes in other environments.

There is also a need for a bioremediation process in contaminated areas, such as crude oil production sites, that will provide reasonably rapid biodegradation of the contaminant, with minimal effect on soil reuse (e.g., minimal or no reduction in compressive strength or load bearing capacity). Additionally, since large amounts of organic waste are generated annually from agricultural plantations, animal farms, mills, food processing plants and industrial plants there is a need to find ways to dispose of these wastes in an environmentally friendly way.

There is a long felt need to provide environmentally acceptable compositions and methods that provide solutions of all the aforementioned problems.

OBJECTS OF THE PRESENT INVENTION

It is an object of the present invention to provide a biopesticide compositions and/or biopesticide formulations capable of serving as effective biocontrol agent.

It is another object of the present invention to provide compositions and methods for controlling plant diseases.

It is an object of the present invention to provide novel products having antagonistic activity for controlling plant diseases.

It is another object of the present invention to provide a method for controlling plant diseases using the fermented products of the invention.

It is another further object of the invention to provide effective, inexpensive, and environmentally appropriate compositions and methods for controlling plant diseases caused by plant pathogens and especially plant pathogenic bacteria.

It is yet a further object of the present invention to provide fermented composition useful in promoting plant growth, soil health and bio-controlling.

It is still a further object of the present invention to provide formulations and methods for controlling and suppressing plant pathogens.

It is another object of the present invention to provide compositions useful for treating bud rot in palm trees.

It is still a further object of the present invention to provide compositions for treating infestations of stable flies in fruit trees.

It is an additional object of the present invention to provide compositions for treating waste waters generated in agricultural environments associated with harvesting and processing fruits.

It is still another further object of the present invention to provide compositions and methods useful in agricultural applications as biopesticides.

A still further object of the invention to provide improved products and methods for general bioremediation of soil, including the improvement of soil condition to enhance the ability of soil to support vital plant growth.

An additional further object of the invention is the fermentation and propagation of such fermentation of naturally occurring materials with yeast.

For a better understanding of the invention, its operating advantages and the specific objects attained by its user, reference should be made to the accompanying drawings, examples and descriptive matter in which there are illustrated many embodiments of the invention.

SUMMARY OF THE INVENTION

Figure 1:
FIG. 1 shows an untreated palm tree that is infected with bud rot.
Figure 2:
FIG. 2 shows a treated palm tree that is now free of bud rot.
Figure 3:
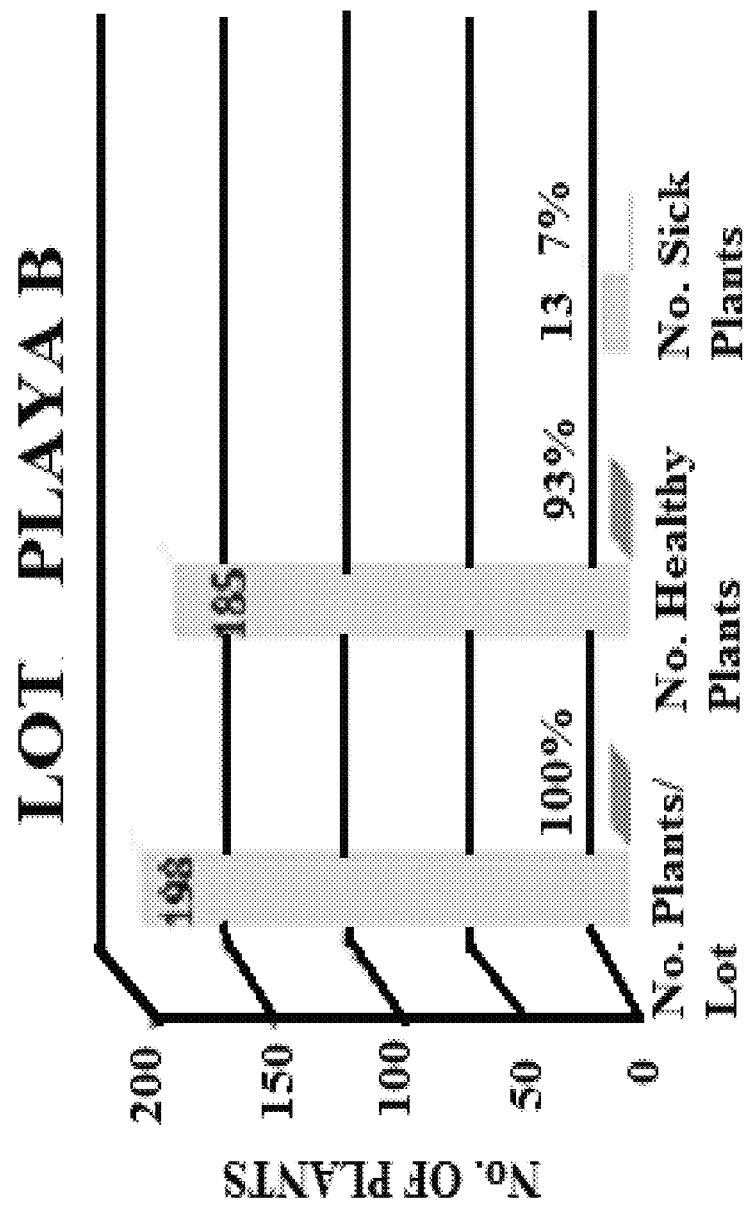
FIG. 3 illustrates the number of healthy plants in a field trial for treating plants infested with mokko.
Figure 4:
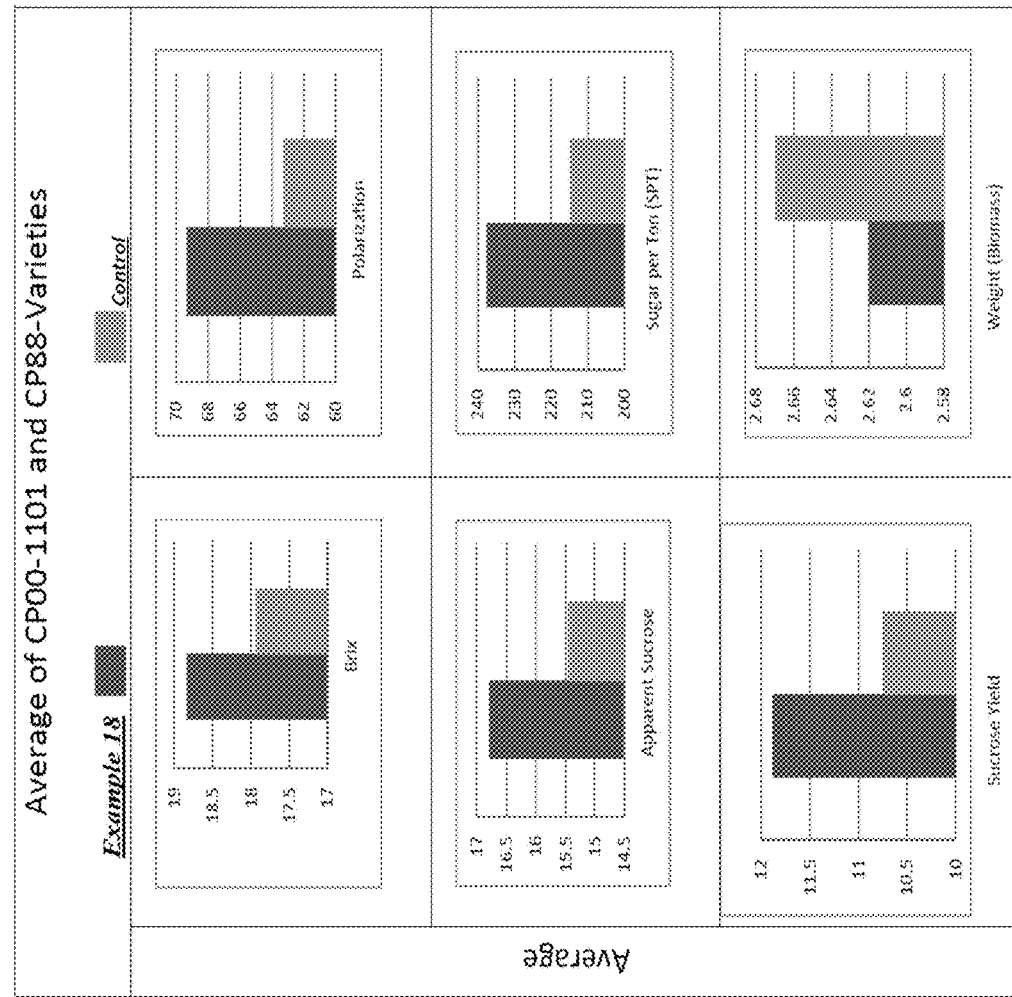
FIG. 4 shows the average results of treating two varieties of sugar cane with the growth promoter/ripener product of Example 18 compared with a control.
Figure 5:
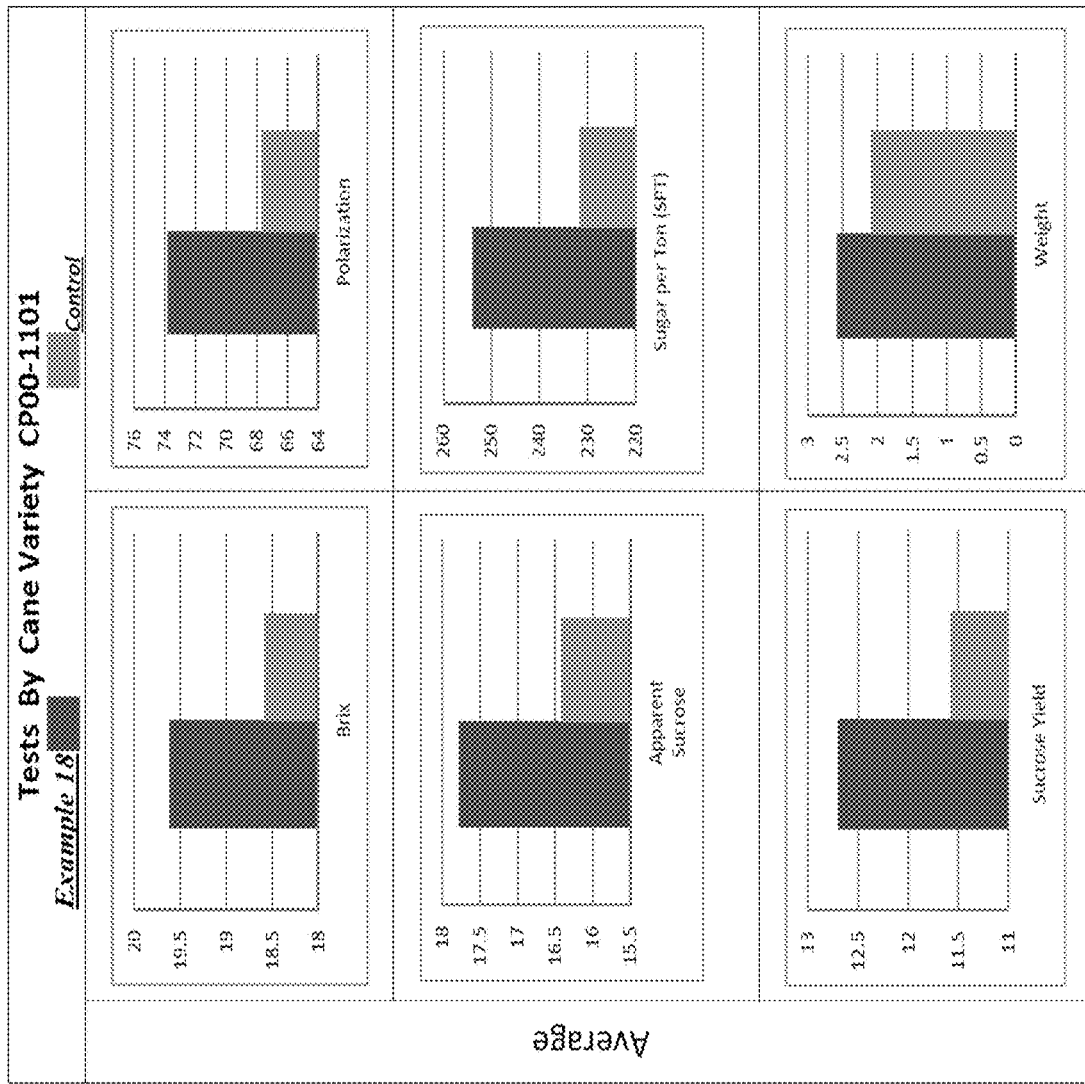
FIG. 5 describes the results of treating sugar cane variety CP00-1101 with the growth promoter/ripener product of Example 18 compared with a control.
Figure 6:
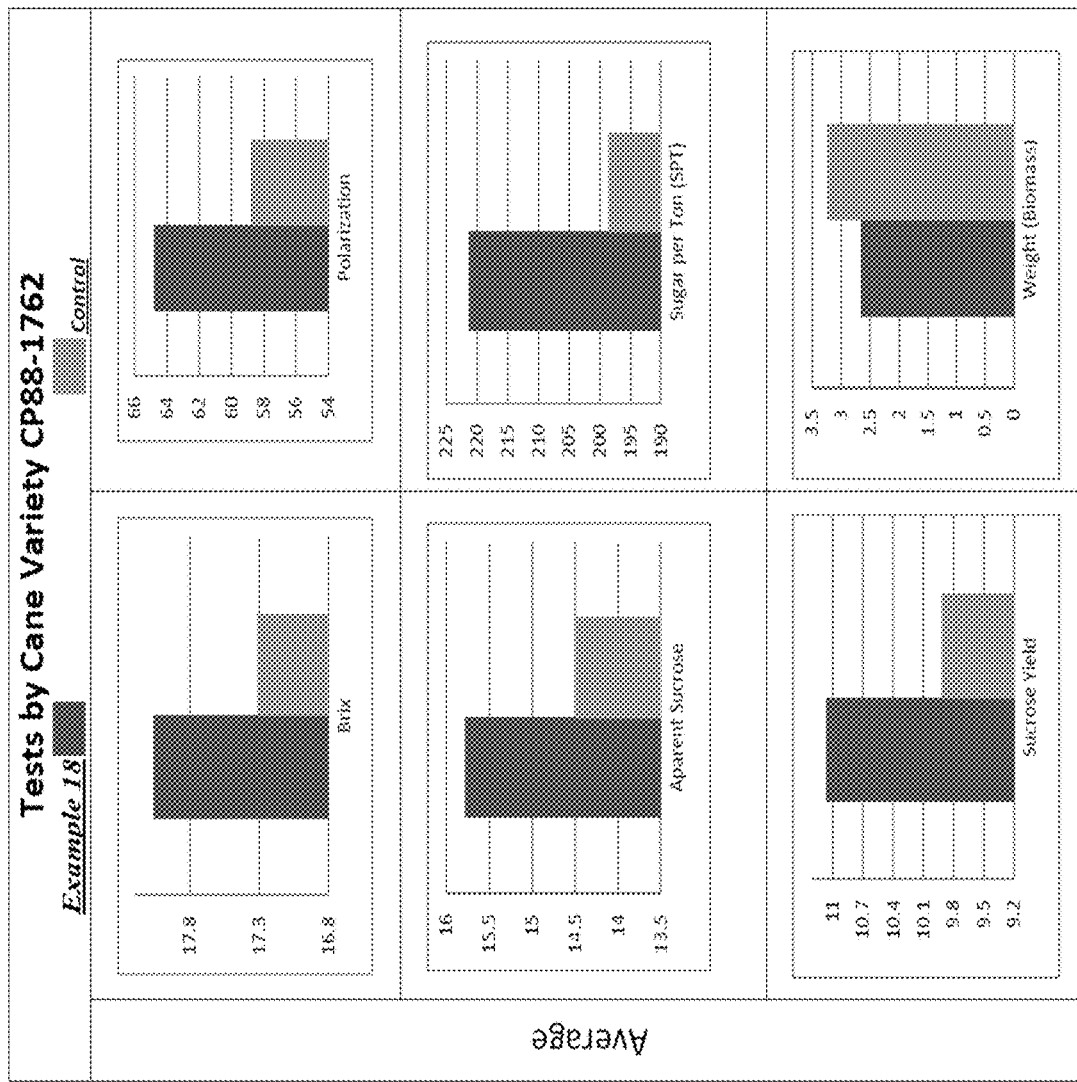
FIG. 6 features the results of treating sugar cane variety CP88-1762 with the growth promoter/ripener product of Example 18 compared with a control.
Figure 7:
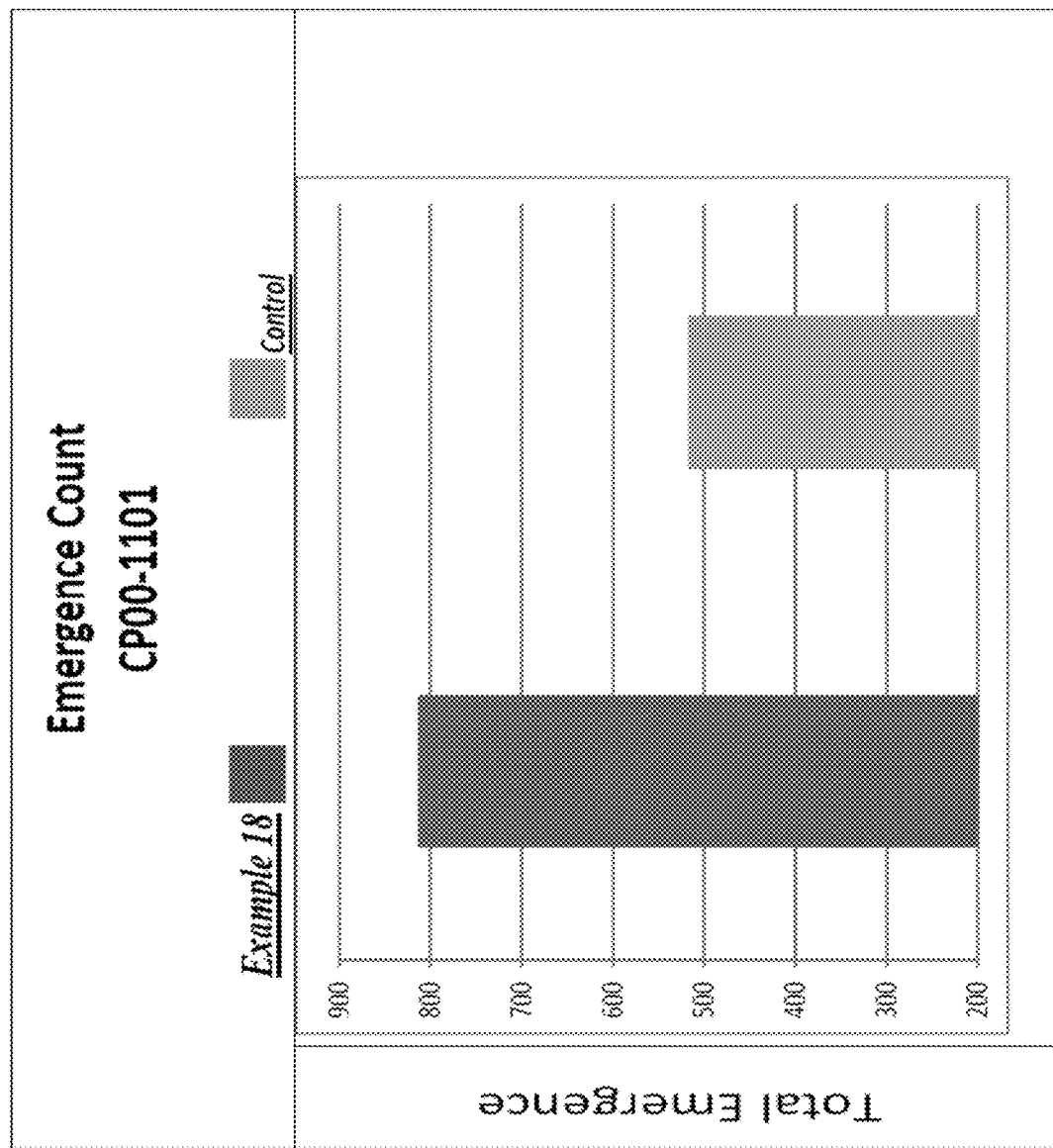
FIG. 7 show the emergence of new sprouts after treating sugar cane variety CP00-1101 with the growth promoter/ripener product of Example 18 compared with a control.

The present invention provides compositions and methods for many agricultural phytosanitary applications. The compositions are particularly useful for the mitigation and control of viruses, bacteria, fungi, insects and other pests, and/or complexes of the aforementioned, including but not limited to the following: *Basidiomycetes, Ustilaginomycetes, Entorrhizomycetidae, Ustilaginomycetidae, Exobasidiomycetidae, Tilletia caries, Uredinio-mycetes (royas), Coleosporium tussilaginis, Puccinia, Cronartium, Hymenomycetes, Exo-basidiales, Exobasidium vaccinii, Auricolariales, Rhizoctonia, Polyporales, Phymatotrichum, Fomitopsis pinicola, Heterobasidion annosum, Agaricales, Armillaria mellea, Armillaria ostoyae, Oomycetes* selected from the group consisting of: *Pythiales, Pythiaceae, Phytophthora, Phytophthora infestans, Phytophthora ramorum, Phytophthora cinnamomi, Phytophthora Palmivora, Pythium Peronosporales, Peronosporaceae, Plasmopara viticola, Peronospora farinosa, Albuginaceae, Albugo candida, Quitridiomycetes, Synchytrium endobioticum* and *Deuteromycetes* selected from the group consisting of: *Rhizosphaera kalkhoffii, Kabatina juniperi*, and *Sirococcus conigenus*.

The compositions of the invention are also useful against bacterial pathogens that attack, consume (in whole or in part), or impede the growth and/or development of plants and/or act as transmission vectors to the plant and/or other plants caused by such bacterial pathogens. The bacterial pathogens include *Agrobacterium, Agrobacterium tumefaciens, Erwinia, Erwinia amylovora, Xanthomonas, Xanthomonas campestris, Pseudomonas, Pseudomonas syringae, Ralstonia solanacearum, Corynebacterium, Streptomyces, Streptomyces scabies, Actinobacteria, Micoplasmas, Spiroplasmas* and *Fitoplasmas.*

The compositions of the invention are also useful for mitigating, controlling and/or eradicating viral pathogens that attack, consume (in whole or in part), or impede the growth and/or development of the plant and/or act as transmission vectors to the plant and/or other plants caused by such viral pathogens. Such viral pathogens include Carlaviridae, mosaic virus of the alamo, Closteroviridae, viruses that attack citrus fruits, Cucumoviridae, Harviridae, dwarf virus attacking prunes, Luteoviridae, Nepoviridae, Potexviridae, potato viruses, Potyviridae, Tobamoviridae, tobacco mosaic virus, Caulimoviridae, cauliflower mosaic virus, viruses that attack wheat as well as other viruses that attack vegetation and crops.

The compositions of the invention are also useful in mitigating, controlling and/or eradicating the following insects: *Hemipteras, Lepidoptera, Coleoptera, Homoptera, Diptera, Thysanoptera, Hymenoptera, Isoptera* and *Aptero.*

The crops and plants that are treated from possible pathogens inflicted by virus, bacteria, fungi, insects and other pests include *Anthocerotae, Musci, Hepaticae, Equisetophyta, Lycopodiophyta, Psilophyta, Pteridophyta* and *Spermatophyta* subdivisions of the Plant kingdom but is not limited to the following families: Poaceae (Wheat, Grains, Cereals), Aracaceae (African Palm), Musaceae (Banana, Plantain, Heliconia), Rubiaceae (Coffee Bean), Fabaceae (Legumes), Malvaceae (Cocoa), Bromeliaceae (Pineapple), Solanaceae (Potato, Chili), Brassicaceae (Brocoli), Asparagaceae (*Yucca*), Agavaceae (Agave), Vitaceae (Grape) and Rosaceae (Strawberry).

The compositions of the invention are for edaphic and foliar applications for a large variety of crops and plants, included but not limited to those listed above, as well as any and all other pathogenic diseases and/or complexes that are encountered in agriculture. By pathogen we define any virus, fungus, bacteria, insect and/or pest or vector that affects the plant detrimentally (biologically or economically). By complex, we define the interaction of one or more of the pathogen(s) to create a disease or detrimental condition (biological or economic) to the plant, animal or microorganism.

The invention further describes the isolation and evaluation of pesticidal, biological, biocontrol, ethno botanical, as well as therapeutic properties of these biopesticide compositions and/or biopesticide formulations obtained from fermenting plants capable of serving as effective biocontrol agents and/or pest control management agents. The products of the invention are useful in the following areas:

Agricultural Nutritional Applications.

Foliar and edaphically applied products used to supplement plant nutritional elements like nitrogen, phosphorous and potassium as well as mineral elements including but not limited to silicium, calcium, magnesium and manganese. These products can be applied to but not limited to the crops and plants listed above.

Bio-Industrial Applications

1. Nourishment and reduction of stress factors of microorganisms in fermentative processes, including yeasts, algae, phyto & zoo plankton, *Lactobacillus* and others, involved in, but not limited to, alcohol fermentations (in all its forms), biofuel production, yeast propagation, and/or production of milk derivatives.

2. Nourishment and reduction of stress factors in the production of micro-, mezzo- and macro-algae, phyto and zooplankton, for the production of proteins, oils, materials, and other organic compounds in aquaculture or biofuel production.

Bio-Remediation Applications (Water and Soils)

1. Degradation of hydrocarbons, toxic chemicals, spilled toxic contaminants, organic and inorganic materials, and mineralization of contaminating compounds that affect soils and/or bodies of water.

2. Removal or control of odors and vectors resulting from the decomposition of organic wastes from industrial processes.

3. Creation of composts, substrates, hummus, soils, and mulches from organic contaminant materials.

4. Creation of suppressive soils inhibiting the growth of harmful pathogens and microorganisms.

Human Health Applications (Inorganic Minerals of the Invention)

Stabilization of stomach pH levels in order to prevent creation of stomach acids, which disrupt the digestive flow, preventing the erosion of the stomach mucus membrane and reducing the incidence of ulcers, gastritis, and reducing conditions which have been linked to stomach cancer. Reduces the number of the *Helicobacter pilori* bacteria in the intestinal track by trapping and elimination through the digestive tract and creating conditions for the increase of beneficial intestinal flora.

Fuel Additive

1. Alcoholic substrates to mix with fuels, achieving the increase in caloric potential (BTUs), reduction of viscosity, and/or homogenizing the flash points of the different hydrocarbon molecules present in the fuel, in order to increase the power and performance, and reduction of contaminant emissions of the different fuels derived from biological processes (biofuels), and petroleum.

2. The reduction of viscosity of petroleum products and biofuels, includes but is not limited to the liquefaction of petroleum and derivatives, oils, bitumen, shale oils, waste oils, and others, expanding their commercial application and/or facilitating their extraction from the field.

3. The reduction of viscosity, together with the efficiency of combustion results in a reduction of carbon particles contributing to the cleaning or cleansing of the engine, fuel lines, exhaust, and other parts of the combustion system coming into contact with the additive.

The invention also presents an alternative product to chemical pesticides, which is a natural organic composition derived from a fermented mixture of plants and carbohydrates. The pesticidal activity of this composition was investigated against *Mycosphaerella fijensis* causing Sigatoka disease in Cavendish (banana), *Ralstonia solanacearum* causing Moko disease in Cavendish (banana), *Colletotrichum gloespoiroides* and *Botryodiplodia theobromae* causing anthracnose in crops and fruits, tomato yellow leaf curl virus (TYLCV) in tomatoes, *Lasiodiplodia theobromae* causing soft rot or fruit rot in crops and fruits, *Fusarium oxysporum* causing Panama wilt in fruits and crops, and many others. The composition is also useful for treating bud rot or crown rot in palm trees as well as diseases in coffee plants.

The invention provides a composition comprising the fermentation product of one or more natural products selected from the group consisting of red beans, peas, white rice, yellow corn and mixtures thereof, an inorganic minerals containing phosphorus, calcium, silicon and titanium and strontium, non-iodized salt, potable water and *Bacillus megaterium*.

The invention is also directed to a biopesticidal composition for treating, mitigating, inhibiting or preventing the development of a plant pathogenic disease comprising the fermentation product of one or more natural products selected from the group consisting of green peas, red beans, yellow corn, white onions, green onions (scalions), *eucalyptus* leaves and/or flowers, green lemon peels and rinds, nettle leaves, *Yucca* leaves, nutmeg (interior part), green lemon peel and rinds, nettle leaves, ruda leaves, wormwood leaves (absinthe), green or red peppers (non-spicy), peeled garlic, green leaves of citronella, red beans, mint green leaves, red tomato leaves and fruit, soya leaves and fruits, celery (leaves and branches), basil (leaves), raw oats in hull, oregano leaves, mata-raton leaves (*Gliricidia sepium* (jacquin)), red beans, horse tail fern (Equisetaceae), plantain leaves, basil oil, garbanzo beans, lentils, barley, citric oil, white rice, salitre, barley (cereal), sorghum, yellow pine sawdust, pine oil, non-iodized sea salt, inorganic minerals containing phosphorus, calcium, silicon and titanium and strontium, potable water and one or more of an inoculant selected from the group consisting of yeast *Saccharomyces cerevisiae*, *Bacillus subtillis* spores, *Bacillus aglomerans* spores, *Bacillus megaterium* spores, *Pseudomanas*, *Azotobacter*, and *Bacillus licheniformis*.

The instant invention also provides a composition and method for bioremediation of environmental materials containing at least one contaminant. The environmental material can be organic (e.g., mulch) and/or inorganic (e.g., sand). The contaminant can be organic (e.g., petroleum hydrocarbons, greases, etc) and/or inorganic (e.g., nitrates).

DETAILED DESCRIPTION OF THE PRESENT INVENTION

Before the present compositions and method for controlling plant diseases are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a composition comprising "an activity" for inhibiting or treating growth of a plant pathogen includes reference to two or more of such activities, reference to "a solvent" includes reference to one or more of such solvents, and reference to "a pathogen" includes reference to one or more of such pathogens.

In describing and claiming the present invention, the following terminology will be used in accordance with the definitions set out below.

As used herein, "plant part" refers to a leaf, stem, root, fruit, seed, tuber, or the like that can be infected or invaded by a plant pathogen.

The soil is intended to mean the medium where the plants are planted.

As used herein, "plant pathogen" refers to a pathogen capable of infecting and/or invading a plant part and causing disease therein.

As used herein, "activity" means a component or components of fermented products that can be extracted therefrom in an aqueous solvent and exerts an effect of mitigating, ameliorating, treating, preventing and inhibiting growth of a plant pathogen when applied to a plant part and/or soil.

The term "bactericidal", as used hererin, refers to the ability of a substance to increase mortality or inhibit the growth rate of bacteria.

Biological control: As used herein, "biological control" is defined as control of a pathogen or insect or any other undesirable organism by the use of a second organism. An example of a known mechanism of biological control is the use of enteric bacteria that control root rot by out-competing fungi for space on the surface of the root. Bacterial toxins, such as antibiotics, have been used to control pathogens. The toxin can be isolated and applied directly to the plant or the bacterial species may be administered so it produces the toxin in situ.

The terms "treat," "treatment," and grammatical variants thereof, when used herein with reference to an organic waste refers to contact of the organic waste with a disclosed composition which results in degradation or conversion of the chemical compounds contained within the organic waste. For example, the treatment may involve degradation of the chemical compounds so as to neutralize odorous compounds contained therein and render the organic waste odorless, or conversion of the carbon-compounds or nitrogen fixation so as to increase the nutrient level of the organic waste. The degradation or conversion may be, for example, effected by the enzymes that are secreted by the one or more microorganisms in the disclosed composition. Exemplary enzymes include, but are not limited to, cellulases, amylases, xylanases, galactanases, mannanases, arabanases, $\beta$-1,3-1,4-glucanases, glucosidases, xylosidases, lipases, hemicellulases, pectinases, proteases, pectin esterases, and the like.

As used herein, bioremediation is one type of decontamination; other types of decontamination are chemical treatment, mechanical removal, and heat reduction. As used herein, a contaminant is any material that imparts an undesirable, but not necessarily toxic, property to the environmental material; the terms "contaminant" and "pollutant" are used synonymously. As used herein, the term "environmental material" refers to material to be bioremediated, and is used synonymously with the terms "matrix", "waste", "debris", and "spoils". Once a bioremediation composition is provided, the material is referred to herein as "treated material" or "bioremediated material", notwithstanding that complete bioremediation may require subsequent treatment, subsequent treatment time, etc. Any level of contaminant reduction from untreated material is encompassed by the disclosed bioremediation method; bioremediation to an extent that no contaminant(s) are detected (e.g., 100% bioremediation) may but need not occur.

Culturing: The term "culturing", as used herein, refers to the propagation of organisms on or in media of various kinds.

Composition: A "composition" is intended to mean a combination of active agents and another compound, carrier or composition, inert (for example, a detectable agent or label or liquid carrier) or active, such as a pesticide.

Effective amount: An "effective amount", as used herein, is an amount sufficient to affect beneficial or desired results. An effective amount can be administered in one or more administrations. In terms of treatment, inhibition or protection, an effective amount is that amount sufficient to ameliorate, mitigate, prevent, stabilize, reverse, slow or delay progression of the target infection or disease states.

Fungicidal: As used herein, "fungicidal" refers to the ability of a substance to decrease the rate of growth of fungi or to increase the mortality of fungi.

Fungus: The term "fungus" or "fungi", as used herein, includes a wide variety of nucleated spore-bearing organisms that are devoid of chlorophyll. Examples of fungi include yeasts, molds, mildews, rusts, and mushrooms.

Insecticidal: As used herein, 'Insecticidal' refers to the ability of a substance to increase mortality or inhibit the growth rate of insects or their larvae.

Microbicidal: "Microbicidal", as used herein, refers to the ability of a substance to increase mortality or inhibit the growth rate of microorganism.

Mutant: As used herein, the term "mutant" or "variant" refers to a modification of the parental strain in which the desired biological activity remains similar to that of the parental strain. Mutants or variants may occur in nature without the intervention of man. They also are obtainable by treatment with or by a variety of methods and compositions known to those of skill in the art. For example, parental strains may be treated with a chemical such as N-methyl-N'-nitro-N-nitrosoguanidine, ethylmethanesulfone, or by irradiation using gamma, x-ray, or UV-irradiation, or by other means well known to those practiced in the art.

Nematocidal: The term "nematocidal", as used herein, refers to the ability of a substance to increase mortality or inhibit the growth rate of nematodes.

Pesticidal: The term "pesticidal", as used herein, refers to the ability of a substance to decrease the rate of growth of a pest, i.e., an undersired organism, or to increase the mortality of a pest.

The products of the invention are useful for many applications in the field of agronomy, environmental remediation, ecology, and many other fields where a green product is desirable. The products of the invention control, mitigate and induce resistance to many pathogens.

In the agricultural field, the products are useful for controlling viruses, bacteria, fungi, insects and other pests, or pest complexes, as defined herein, through edaphic and foliar applications. Specific diseases for which the products are effective include Bud Rot, Crown Rot, Red Ring, Pudricion de Cogollo, Lethal Yellowing and other pathogenic diseases or complexes in all species of palms, including but not limited to ornamental palms, coconut palms, date palms, African Oil Palms, and hybrids thereof.

Other diseases that are treated with the products of the invention include:

1. Moko, Black and Yellow Sigatoka, *Erwinia*, Nematodes, Picudo, and other pathogenic diseases or complexes in all species of banana and plantains, heliconias, birds of paradise, and other musaceas, and hybrids thereof.

3. Rice Blast, Panicle Blight, *Fusarium*, Vaneo de Arroz, mosaic virus, and other pathogenic diseases or complexes in all species of cereal or grains, including but not limited to rice, wheat, corn, sorghum, and hybrids thereof.

Other crops and plants which are included for treatment with the products of the invention include coffee, cacao, sugar cane, flowers and other ornamental plants, fruits, vegetables, and legumes, including but not limited to soy, peanuts, tomatoes, avocadoes, mangoes, pears, row crops, pastures and grasses, citrus, beets, berries, root and tuber vegetables and/or crops The products of the invention are also useful biopesticides against all manner of insects or other arthropods that attack, consume (in whole or in part), or impede the growth and/or development of the plant, animal or microorganism, and/or act as transmission vectors to the plant, other plants and/or other animals or humans.

The products of the invention are useful against arthropods which can be effectively repelled or eradicated by the present compositions include blood-sucking insects such as mosquitoes (*Culex* spp.) represented by *Anopheles* spp. such as *Anopheles albimanus*, etc., *Aedes* spp. such as *Aedes aegypti, Aedes albopictus*, etc., house mosquitoes (*Culex* spp.) such as common mosquito (*Culex pipiens pallens*), *Culex tritaeniorphynchus*, etc., black flies (Simuliidae), stable flies (Stomoxyidae), sand flies (Psychodidae), bitting midge, etc.; and Ixodidae such as *Amblyomma, Rhipicephalus, Dermacentor, Ixodes, Haemaphysalis, Boophilus*, etc.

Other uses for the products of the invention include aquaculture of fish, shrimp, algae, phyto and zoo plankton, removal of toxic chemical traces from soils, creation of suppressive soils inhibiting the growth of harmful pathogens and microorganisms, and any and all other pathogenic diseases and/or complexes that are encountered in agriculture. By pathogen we mean any virus, fungus, bacteria, insect and/or pest or vector that affects the plant and soil detrimentally (biologically or economically). By complex, we define the interaction of one or more of the pathogen(s) to create a disease or detrimental condition (biological or economic) to the plant, animal or microorganism.

The products of the invention also find use in bio-industrial applications such as:

1. Nourishment and reduction of stress factors of microorganisms in fermentative processes, including yeasts, algae, phyto and zoo plankton, lacto-*bacillus* and others, involved in, but not limited to, alcohol fermentations (in all its forms), yeast propagation, and/or production of milk derivatives.

2. Nourishment and reduction of stress factors in the production of micro-, mezzo- and macro-algae, phyto and zoo plankton, for the production of protein, oils, materials, and other organic compounds.

3. Bio-remediation applications such as degradation of hydrocarbons, toxic chemicals, organic and inorganic materials, and mineralization of contaminating compounds that affect soils and/or bodies of water, removal or control of odors and vectors resulting from the decomposition of organic wastes from industrial processes, creation of composts, substrates, hummus, soils, and mulches from organic contaminant materials, in improving human health, as fuel additives, as alcoholic substrates to mix with fuels, achieving an increase in caloric potential (BTUs), reduction of viscosity, and/or homogenizing the flash points of the different hydrocarbon molecules present in the fuel, in order to increase the power and performance, and reduction of contaminant emissions of the different fuels derived from biological processes (biofuels), and petroleum.

The products of the invention can also be used for reduction of viscosity of petroleum products and biofuels, includes but is not limited to the liquefaction of petroleum and derivatives, oils, bitumen, shale oils, waste oils, and others, expanding their commercial application and/or facilitating their extraction from the field. The reduction of viscosity, together with the efficiency of combustion results in a reduction of carbon particles contributing to the cleaning or cleansing of the engine, fuel lines, exhaust, and other parts of the combustion system coming, into contact with the additive.

The invention provides multiple products which find use in agriculture as fungicides, bactericides, antiviral, as well as in green bioremediation and water purification.

In its broadest aspect the invention provides a composition for treating, inhibiting or preventing the development of a plant pathogenic disease comprising the fermentation product of one or more natural products selected from the group consisting of green peas, red beans, yellow corn, white onions, green onions (scalions), *eucalyptus* leaves and/or flowers, green lemon peels and rinds, nettle leaves, *yucca* leaves, nutmeg (interior part), green lemon peel and rinds, nettle leaves, ruda leaves, wormwood leaves (absinthe), green or red peppers (non-spicy), peeled garlic, green leaves of citronella, red beans, mint green leaves, red tomato leaves and fruit, soya leaves and fruits, celery (leaves and branches), basil (leaves), raw oats in hull, oregano leaves, mata-raton leaves (*Gliricidia sepium* (jacquin)), red beans, horse tail fern (Equisetaceae), plantain leaves, basil oil, garbanzo beans, lentils, barley, citric oil, white rice, salitre, barley (cereal), sorghum, yellow pine sawdust, pine oil, non-iodized sea salt, inorganic minerals containing phosphorus, calcium, silicon and titanium and strontium, potable water and one or more of an inoculant selected from the group consisting of yeast *Saccharomyces cerevisiae*, *Bacillus subtillis* spores, *Bacillus aglomerans* spores, *Bacillus megaterium* spores spores, *Pseudomonas*, *Azotobacter*, and *Bacillus licheniformis*. The composition is particularly useful as demonstrated in the examples of the invention for uses is biopesticides, bioremediation, water purification, aquaculture and all applications where agricultural crops and soil are threatened by all pests known in nature. Additionally, the compositions of the invention are also particularly useful in controlling odor of agricultural waste and waste waters.

It should be noted that numerous species of microorganisms can be used in making the fermented compositions of the invention. They include *Bacillus* sp. microorganisms, *Pseudomonas* sp. microorganisms, *Bifidobacterium* sp. microorganisms, and *Lactobacillus* sp. microorganisms, with one of *Streptomyces* sp. microorganisms or *Corynebacterium* sp. microorganisms. Other microroganisms include *Streptomyces pactum*, *Corynebacterium striatum*, *Bacillus pumilus*, *Bacillus stearothermophilus*, *Bacillus brevis*, *Bacillus cereus*, *Bacillus subtilis*, *Bacillus sphearieus*, *Bacillus licheniformis*, *Pseudomonas alcaligenes*, *Pseudomonas marinoglutinosa*, *Bifidobacterium thermophilus*, *Lactobacillus casei*, *Lactobacillus planatarum* and *Lactobacillus fermentus*.

One of the products of the invention also acts as an enhancer of other fermentation products. The enhancer is a product comprising the fermentation product of one or more natural products selected from the group consisting of red beans, peas, white rice, yellow corn and mixtures thereof, an inorganic mineral containing phosphorus, calcium, silicon and titanium and strontium, non-iodized salt, potable water and *Bacillus Megaterium*. The above enhancer can be combined with the following products to produce very useful compositions for use as agricultural bio-pesticides and in bioremediation. The enhancer is combined with:

(1) a fermentation product of one or more natural products selected from the group consisting of white onions, green onions (scalions), *eucalyptus* leaves and/or flowers, green lemon peels and rinds, nettle leaves, *yucca* leaves, nutmeg (interior part), inorganic minerals containing phosphorus, calcium, silicon and titanium and strontium, water and *Bacillus subtillis*;

(2) the fermentation product of one or more natural products selected from the group consisting of green onion (scalions), white onions, green lemon peel and rinds, nettle leaves, ruda leaves, wormwood leaves (absinthe), *eucalyptus* (leaves and/or flowers), nutmeg (interior part), inorganic minerals containing phosphorus, calcium, silicon and titanium and strontium, water and *Bacillus aglomerans*;

(3) the fermentation product of one or more natural products selected from the group consisting of green or red peppers (non-spicy), peeled garlic, green leaves of citronella, red beans, mint green leaves, nettle leaves, red tomato leaves and fruit, ruda leaves, inorganic minerals containing phosphorus, calcium, silicon and titanium and strontium, water and *Pseudomonas*;

(4) the fermentation product of one or more natural products selected from the group consisting of raw oats in hull, barley (cereal), *yucca* leaves, white onion, green lemon peel and rinds, green leaves of citronella, inorganic minerals containing phosphorus, calcium, silicon and titanium and strontium, water and *Bacillus megaterium*;

(5) a fermentation product of one or more natural products selected from the group consisting of soya leaves and fruits, celery (leaves and branches), basil (leaves), inorganic minerals containing phosphorus, calcium, silicon and titanium and strontium, water, *Saccharomyces cerevisiae* and *Bacillus megaterium*; and (6) fermentation product of one or more natural products selected from the group consisting of oregano leaves, soya (leaves and fruits), celery leaves and branches, basil leaves, salitre, inorganic minerals containing phosphorus, calcium, silicon and titanium and strontium, water, and *Bacillus megaterium*.

Another product of the invention is a composition comprising the fermentation product of one or more natural products selected from the group consisting of mata-raton leaves (*Gliricidia sepium* (jacquin)), red beans, yellow corn, white rice, basil oil, non-iodized salt, inorganic minerals containing phosphorus, calcium, silicon and titanium and strontium, water, *Saccharomyces cerevisiae*, and *Azotobacter*.

An additional product of the invention is a composition comprising the fermentation product of one or more natural products selected from the group consisting of garbanzo beans, lentils, barley, oat hulls, citric oil, non-iodized salt, inorganic minerals containing phosphorus, calcium, silicon and titanium and strontium, water, *Saccharomyces cerevisiae*, *Bacillus megaterium*, *Bacillus subtillis* and *Bacillus licheniformis*.

The invention further provides a bio-derived composition useful in controlling agricultural pests and for bioremediation of waste waters comprising: (a) a product of fermenting with 0.01-0.10% by weight of Baker's yeast; a formulation comprising: (i) 1-10% by weight Green Peas, (ii) 1-10% by weight Red beans, (iii) 1-10% by weight Yellow corn, (iv) 1-10% by weight Sorghum, (v) 5-10% by weight Yellow pine sawdust, (vi) 1-10% by weight Pine Oil, (vii) 0.1-0.5% by weight non-iodized sea salt; and (b) 1-20% by weight of a mixture of spores comprising *Bacillus subtillis* spores, *Bacillus aglomerans* spores and *Bacillus megaterium* spores.

The invention further provides a bio-degreasing composition comprising the fermentation product of one or more natural products selected from the group consisting of garbanzo beans, lentils, barley, oat hulls, citric oil, non-iodized salt, inorganic minerals containing phosphorus, calcium, silicon and titanium and strontium, water, *Saccharomyces cerevisiae*, *Bacillus megaterium* and *Pseudomonas*.

The minerals used in the fermentation processes of the invention include about 10.00-20.00 ppm Na, 5,000.00-20,000.00 ppm Mg, 100.00-500.00 ppm Al, Si present as silicate of the many elements in the mineral, 20.00-60.00 ppm P, 10.00-30.00 ppm K, 30,000.00-200,000.00 ppm Ca, 50.00-550.00 ppm Ti, 10.00-45.00 ppm Mn, 300.00-1500.00 ppm Fe, 0.20-1.50 ppm Co, 0.5-3.00 ppm Ni, 0.30-5.00 ppm Cu, 0.50-4.00 ppm Zn, 0.5-5.00 ppm As, 200.00-1,000.00 ppm Sr and 5.00-35.00 ppm Ba, as well as many other trace elements commonly found in those minerals.

The products of the invention are made by the following process:

1. The natural ingredients are cut or reduced to size and mixed with water.
2. The resulting mixture from the previous step is then heated to a boil.
3. The mixture is then allowed to cool to room temperature.
4. A sample is taken from top of the mixture obtained in step (3) above, and checked so that the sample does not contain any solid.
5. Then the yeast *Saccharomyces cerevisiae* (Fleischman brand) is added to the 500 ml sample taken in the previous step (4), mixed slowly and manually to the full incorporation of yeast.
6. The mixture from the previous step is added to the rest of the product referenced in step (3) and mixed in gently for about 5 minutes
7. Store product in a cool dry place, for eight days leaving enough space so the gases from the fermentation process can escape. In the presence of the yeast the solids ferment anaerobically, the water also ferments and the top surface is fermented aerobically as well,
8. After the eight days of fermentative storage the product is filtered using a 40 micron mesh filter and using a recirculating pump in order to make sure biofilm that may be present in excess biomass is removed. The product is filtered several times.
9. Recirculate the product with the help of a diaphragm pump through a pipe provided with electromagnetic fields (2-10,000 gauss) and stored in a tank for applying light stimuli. The electromagnetic field is adjusted so all the products from the fermentation are captured by the water molecules in the resulting product. Once everything is complexed with the water then the product is ready for the next step. A typical end point for this step is a reduction in the volatile content of the complex mixture. In the case of dry products, the application would be a different method of application i.e., passed through a tray and exposed to the electromagnetic field.
10. The product is then treated with ultraviolet light of a frequency 240-280 nm to provide an aseptic product. Other frequencies may be used as long as an aseptic product is obtained.
11. After step 10, one could add spores of *Bacillus* microorganisms or a mixture of microroganisms for further fermentation.

Many variations of the process are described in the examples of the invention, accordingly the process as described above should not be construed as limiting the invention.

Another aspect of the invention provides a method for treating, inhibiting or preventing the development of a plant pathogenic disease, comprising applying a composition of the invention in the vicinity of the plant. In a preferred embodiment, the pathogen may be *Aspergillus fumigatus*, *Botrytis cinerea*, *Cerpospora betae*, *Curvularia* sp., *Ganoderma boninense*, *Geotrichum candidum*, *Mycosphaerellafijiensis*, *Phytophthora palmivora*, *Phytophthora ramorum*, *Pythium ultimum*, *Rhizoctonia solani*, *Rhizopus* sp., *Schizophyllum* sp., *Sclerotinia sclerotiorum*, *Verticillium dahliae*, or *Xanthomonas axonopodis*. In another embodiment, the host plant is susceptible to disease caused by *Ganoderma boninense* or *Phytophthora palmivora*. In another embodiment, the host plant is an oil palm plant and the method is effective to inhibit the growth of the plant pathogen. In other embodiments, the method is effective to kill the plant pathogen.

Some embodiments of the invention provide for the composition to be applied to the vicinity or directly to the plant, such as around the roots, stems, trunk, seed, or leaves of the plant, applied onto such parts of the plant, or injected into such parts of the plant. In other embodiments, the composition can be used to treat or sterilize the soil or plant growth medium, by exposing the soil or plant growth medium to the invention compositions, or by direct contact, such as intermixing, with the composition.

The invention also provides a method for treating, mitigating and/or preventing an infestation of stable flies (*Stomoxys calcitrans*) in agricultural fruit farms which method comprises applying to the fruit plant and/or the soil an effective amount of a composition comprising: (a) a product of fermenting a formulation comprising: (i) 1-10% by weight Green Peas, (ii) optionally 1-10% by weight Red beans, (iii) optionally 1-10% by weight Yellow corn, (iv) optionally 1-10% by weight Sorghum, (v) optionally 5-10% by weight Yellow pine sawdust, (vi) optionally 1-10% by weight Pine Oil, (vii) 0.1-0.5% by weight non-iodized sea salt, (viii) 0.01-0.10% by weight of Baker's yeast; and (b) 1-20% by weight of a mixture of spores comprising *Bacillus subtillis* spores, *Bacillus aglomerans* spores and *Bacillus megalerium* spores.

The instant invention further provies a bio-derived composition useful in controlling agricultural pests that infect palm trees comprising: (a) a product of fermenting a formulation comprising: (i) 1-10% by weight Green Peas, (ii) 1-10% by weight Red beans, (iii) 1-10% by weight Yellow corn, (iv) 1-10% by weight Sorghum, (v) 5-10% by weight Yellow pine sawdust, (vi) 1-10% by weight Pine Oil, (vii) 0.1-0.5% by weight non-iodized sea salt, (viii) 0.01-0.10% by weight of Baker's yeast; and (b) 1-20% by weight of a mixture of spores comprising *Bacillus subtillis* spores, *Bacillus aglomerans* spores and *Bacillus megaterium* spores.

The specific palm trees that may be treated are listed in Table 1 below:

TABLE 1

| | |
|---|---|
| *Archontophoenix alexandrae* | king Alexander palm |
| *Arenga* spp. | Dwarf sugar palm |
| *Borassus flabellifer* | Lontar palm |
| *Brahea armata* | blue hesper palm |
| *Brahea edulis* | Guadalupe palm |
| *Butia capitata* | pindo palm |
| *Chamaerops humilis* | European fan palm |
| *Carpentaria* spp | *Carpenteria* palm |
| *Chamaedorea* | *elegans* parlor palm |
| *C. erupens* | bamboo palm |
| *C. seifrizii* | reed palm |
| *Chrysalidocarpus lutescens* | areca palm |
| *Coccothrinax argentata* | silver palm |
| *C. crinita* | old man palm |
| *Cocos nucifera* | coconut palm |
| *Elaeis guineensis* | African oil palm |
| *Howea forsterana* | kentia palm |

TABLE 1-continued

| | |
|---|---|
| *Livistona rotundifolia* | round leaf fan palm |
| *Neodypsis decaryi* | triangle palm |
| *Normanbya normanbi* | Queensland black |
| *Pinanga insignis* | |
| *Phoenix canariensis* | Canary Island date |
| *Ptychosperma macarthuri* | Macarthur palm |
| *Rhopalostylis* spp | shaving brush p. |
| *Roystonea elata* | Florida royal palm |
| *R. regia* Cuban | royal palm |
| *Sabal* spp | Cabbage/palmetto |
| *Syagrus romanzoffiana* | queen palm |
| *Trachycarpus fortunei* | windmill palm |
| *Trythrinax acanthocoma* | spiny fiber palm |
| *Washingtonia filifera* | petticoat palm |
| *W. robusta* | Washington/Mexican fan palm |

As explained above, there are many pathogens that can cause bud rot of palm trees. Some of the common causes are *Phytophthora palmivora, Thielaviopsis paradoxa* and bacteria. Regardless of the pathogen causing the disease, the symptoms and treatment are the same.

When a palm tree initially gets infected with bud rot, the first symptoms that become visible are: discoloration and wilting of the spear (new main) leaf and wilting and discoloration of the newer fronds (leaves). The yellowing and wilting is normally from the inner part of the leaf, outwards. In severe cases of disease the main frond or spear leaf can be easily pulled from the bud. In tall palms, where the terminal bud (top point where new growth emerges) cannot be seen from the ground, the early symptoms of palm bud rot are often missed. Often the disease onset is not noticed until new frond growth has stopped and the crown begins to appear to be shrinking or loses its top and appears flat. In cases such as this, often the terminal bud has died, and no new fronds are produced. Existing fronds will remain green for a few months as the tree slowly dies.

Palm bud rot caused by bacterial infections is often associated with cold damage and stress placed on the tree by exposure to cold temperatures. When a palm tree is exposed to cold damage, to prevent the possible onset of palm bud rot the tree should be treated with the product of Examples 1, 5, 6 or 8. Immediately after cold damage or damage from other bud rot causing agents such as from *Phytoptora palmivora* the terminal bud should be sprayed, and then repeated every 10 to 14 days for a series of 4 treatments. It is best not to wait until palm bud rot symptoms emerge. Avoid pruning or removing damaged fronds, as this will place more stress on the tree and increase the potential for other bacterial or fungal infections to enter the tree.

When treating and preventing palm bud rot it is important to realize that palm trees have only one terminal bud from which all new growth emerges. Unlike most trees, such as maple and apple trees which have many points where new growth emerges, palms rely exclusively on their single terminal bud. If the terminal bud or heart becomes diseased or freezes during cold periods and dies, the tree will not be able to put out any new leaf growth and will die. That is why regular monitoring of the terminal bud and preventative care are vital to maintaining a healthy palm tree.

Recommended Steps to Treat Palm Bud Rot

It is always best to take steps to prevent the onset of Palm Bud Rot. Preventative steps should be taken if a palm tree has experienced cold damage or palm bud rot has been identified in the local area. As a preventative treatment, spay the tree's terminal bud with the products of the invention exemplified in Examples 5, 6 or 8 and repeat the treatment every 10 to 14 days, for 3 to 4 treatments, or as necessary.

If a palm tree is already showing symptoms of palm bud rot, immediately treat the tree with the products of Examples 5, 6 or 8, focusing most attention towards the terminal bud. Repeat the spraying every 7 days as necessary. Once a tree is infected with bud rot, it usually dies, but its chances of survival can increase the earlier it is treated with the formulations of the invention. The products of Examples 5, 6 and 8 can also reverse bud rot, and also induce the natural resistance of the palm to the complex disease.

In a further aspect of the invention, the compositions of the invention are useful for treating the rice tarsonemid mite, *Steneotarsonemus spinki* which was first recorded in Baton Rouge, La., USA in 1960. It has been recognized as an important rice pest in several Asian countries such as China, India, Taiwan, Korea, Philippines, and Thailand. The mite was detected in Cuba in 1997 causing severe yield losses, and subsequently was reported in the Dominican Republic, Haiti, Nicaragua, Costa Rica, and Panama causing 30 to 90% yield reduction. The mite was detected in Colombia in 2005 but in low populations with no significant yield reductions. Larvae and adults of *S. spinki* feed on the rice plant tissue causing browning of leaf sheaths and grain hulls. The main damage is caused in association with the bacterial panicle blight pathogen (*Burkholderia glumae*) and detected during panicle emergence resulting in symptoms known as empty head or grain sterility. The products of examples 1, 5, 6, 7 and 8 are particularly useful in combating this disease encountered in rice.

The rice tarsonemid mite is normally found associated with the fungus *Sarocladium oryzae* and recently was found in association with the bacterium *Burkholderia glumae*, the causal agent of bacterial panicle blight in Panama (2005 and 2006) and Colombia (2007), where the incidence of affected plants (grain sterility and discoloration) reached 100% causing yield losses above 80%. In the U.S., the mite has recently (August 2007) been identified in Alvin, Tex. at the RiceTec research facility, the Texas A&M/USDA ARS facility in Beaumont, Tex., and at the winter nursery research facilities in Lajas, Puerto Rico. The locations where the mite has been found are under strict quarantine restriction. The restriction limits access and the infected plants are being sprayed with a series of products of the invention (Examples 1, 5, 6, 7, and 8) over a 6 week period. Areas were inspected for the mite following treatment.

The life cycle (egg to adult) of the mite takes 3-10 days depending on the temperature and relative humidity. An adult female lays about 60-75 eggs in 10-15 days and 48 to 55 generations can be completed in a year. The main host of the mite is the rice plant. The optimal conditions for the growth and reproduction of the mite are 25-27 C and relative humidity above 80%. Periods of sunny days and low rain favor mite development but low relative humidity and heavy rains increase mortality reducing the mite population. The mite can be disseminated on seeds, by wind, water, insects, agricultural machinery, and survives on plant debris after harvesting. It can be detected on young plants when infested seed is planted or if neighboring fields were heavily infested. The milky stage is preferred by the mite for feeding and its reproduction. The mite is mainly detected in the inner part of the leaf sheath where high populations of nymphs and adults can be found. It is mainly found in the upper part of the sheath close to the leaf, but can also be found in the middle or lower part of the sheath. Small brown spots on the sheath are indications of mite presence. The mite can also be found on the endosperm and the inner part of the hulls. It is sometimes difficult to detect in the field because of its transparent appearance, small size (195-265 μm×92-109

μm), and preferred location in the inner part of the sheaths. However, a 20× magnifier can be used for detecting individual mites or detecting colonies which can reach populations of 300 mites/cm2.

Heavy infestations of the mite occur during the rice reproductive stage helping to disseminate the bacterium *B. glumae* causing erect or deformed panicles and turning the surface of grain brown to dark black. Affected panicles contain a mixture of green, tan, and brown kernels. The mite apparently injects a toxin that can cause grain deformation. Grain quality and milling can be affected. Leaf sheaths exhibit browning symptoms. All symptoms observed are similar to those caused by the bacteria panicle blight and sheath rot pathogen, which are normally found in association with the mite.

The products of the invention exemplified in examples 1, 5, 6, 7, and 8 are particularly effective in the control the rice tarsonemid mite avoiding broad dissemination of the bacterium *B. glumae*. To prevent the introduction of the mite into a new crop, it is necessary to destroy plant debris after harvesting infested fields, and disinfect the rice seed before planting. In the tropics, planting dates should be modified to avoid favorable conditions for mite development during the most susceptible plant development stage of panicle formation and emergence. Differences in resistance to *S. spinki* have been observed among rice varieties, however results are not conclusive. Cultural practices favoring a healthy crop development such as proper nitrogen fertilization, low seeding rates, destruction of plant residues, good land preparation and leveling and adequate water management help to reduce the problem.

The invention further provides bioremediation processes that are targeted and include the deliberate use of the biological, or respiratory, processes to degrade, consume, break down, transform, metabolize, and/or remove contaminants from a treatment zone that is associated with a contaminated region and may be performed both in situ and/or ex situ. In situ bioremediation includes treating the contaminated material without removal from its current, existing, or natural location, while ex situ bioremediation includes removal of the contaminated material from its current, existing, or natural location for treatment at a different site. The bioremediation processes of the invention include the introduction of reactants, such as oxidants and/or nutrients, into the treatment zone to enhance, assist, augment, stimulate, and/or promote the growth of native microorganisms that are already present within the contaminated region and are termed bio-stimulation processes, while bioremediation processes that include the introduction of non-native microorganisms into the treatment zone, with or without the introduction of oxidants and/or nutrients, are termed bio-augmentation processes.

For bioremediation to occur, the contaminated region must include a microbial population that is adapted to metabolize a contaminant, as well as an energy source, a carbon source, an electron acceptor (or oxidant), nutrients, and suitable environmental conditions. The microbial population may include native microbes and/or may include specialized microbes that may be added to the treatment zone during a bio-augmentation process. The contaminant is typically utilized by the microbial population as both the energy source and the carbon source, providing the mechanism by which the bioremediation processes may decrease a contaminant concentration within the treatment zone.

The bioremediation formulations of the invention may include both active and inactive components. The active components may refer to components of the bioremediation formulation that are actively utilized during microbial respiration and/or components of the bioremediation formulation that actively participate in the delivery of the bioremediation formulation to the microorganisms, contaminant, treatment zone, and/or contaminated region. In contrast, inactive components of the bioremediation formulations of the invention are not actively utilized during microbial respiration and/or components of the bioremediation formulation that do not actively participate in the delivery of the bioremediation formulation to the microorganisms, contaminant, treatment zone, and/or contaminated region.

The invention further provides a method for treating an organic industrial waste to degrade the waste, which comprises: (a) providing a fermented product according to Example 1 and (b) adding the fermented product of Example 1 along with a diluent liquid to the industrial waste in a treatment plant, a lagoon, a tank or a soil, wherein the waste is degraded.

Organic waste that may be treated using the disclosed processes and composition include, but are not limited to agricultural waste, food waste, organic refuse, mill effluent, municipal waste, sewage, sludge, animal waste, and industrial waste. Exemplary agricultural wastes include, but are not limited to, oil palm empty fruit bunch (EFB), palm decanter cake slurry, olive husk, corn cob, coffee bean husk, rice husk, rice straw, spent mushroom compost, palm foliage, palm trunk, palm kernel shells, palm fiber, farm effluent, slaughterhouse waste, flower cuttings, spent flower compost, wheat straw, fruit waste, vegetable waste, and the like. Exemplary animal wastes include, but are not limited to, dead animals, animal feather, animal parts (such as animal intestines), and animal manure such as poultry manure, cow manure, goat manure, horse manure, sheep manure, and swine manure. Mill effluent may be, for example, palm oil mill effluent (POME) and POME sludge.

The organic waste to be treated in the disclosed process may be selected based on criteria such as availability due to for example geographical or seasonal variability, cost, suitability, desired product and product properties, and the like. For example, in palm oil producing regions, about 8 million tons of empty fruit bunch (EFB) are generated annually, and hence provides an abundant source of organic waste that can be treated using the disclosed process to at least partly convert the EFB into useful organic fertilizer. Similarly, a typical food processing plant can generate between about 1.5 to about 2 tons of sludge per day while a poultry slaughterhouse can generate about 300 $m^3$/day of wastewater, which result in abundant sources of organic waste for use in the disclosed process.

A single type of organic waste may be used in the disclosed process, or any combination of more than one type of organic waste may be used. For example, EFB may be used together with chicken manure, or food waste may be used together with POME sludge. Other exemplary combinations of organic wastes include, but are not limited to, a combination of chicken manure with dead chickens, a combination of chicken manure with chicken feathers, a combination of EFB with chicken manure, a combination of EFB with chicken manure and POME, and a combination of EFB and POME sludge.

Once a product of the invention has been prepared (i.e., Example 1), it is ready to be applied to the organic waste. For example, if the organic wastes are contained in a lagoon, the product can be sprayed onto the surface of the lagoon or otherwise mixed with the contents of the lagoon for obtaining good coverage of the lagoon. The amount of product that should be added to the lagoon is easily determined by a person of ordinary skill in the art without the need for undue experimentation. Addition of an appropriate amount of product will result in vigorous production of gas as the bacteria metabolize the wastes. Further, the bacteria will substantially control the odors associated with the lagoon within two to four weeks or less time. Addition of an excess of the product of the invention will result in solids from the floor of the lagoon being raised to the surface of the lagoon due to the large amount of gas being produced by the bacteria. This condition is sometimes termed being "upside down." Remedies for an upside down lagoon include (1) doing nothing, wherein the production of gas by the bacteria will gradually diminish and permit the solids to sink to the lagoon floor again, and (2) adding even more product to the lagoon, wherein the solids will be further metabolized by the bacteria and will sink to the floor of the lagoon. The production of gas by the bacteria added to the lagoon results in mixing of the contents of the lagoon, which aids in mixing of the bacteria with the wastes. Since wastes will generally continue to be added to the lagoon, it is necessary to periodically add fresh product to the lagoon.

The fermentation products of the invention can also be used as ripeners and growth stimulants. A pearticular composition that provides this effects includes by weight percent 10% Horse Tail Fern (Equisetaceae), 10.0% Plantain leaves, 2.0% White Onion, 2.0% Nettle leaves, 2.0% Eucalyptus leaves and flowers, 2.0% Composition of Example 3, 71.49% Potable Water and the composition also includes 0.10% *Saccharomyces Cerevisiae*.

The following examples are intended to demonstrate the usefulness of preferred embodiments of the present invention and should not be considered to limit its scope or applicability in any way.

In all of the examples below where microorganisms are used i.e., *Bacillus* or others, the typical starting colony forming units (CFU) per gram is $1 \times 10^{10}$ CFU/gram and when the process is finished the CFU per gram is $1 \times 10^{8}$ CFU/gram.

Example 1

A product having the composition as shown in Table 2 below is made by the method shown below.

TABLE 2

| Ingredients | | Percent by Wt (%) | Amount (Kg) |
|---|---|---|---|
| 1. Green Peas | | 2.5 | 1.5 |
| 2. Red beans | | 2.5 | 1.5 |
| 3. Yellow corn | | 2.5 | 1.5 |
| 4. *Sorghum* | | 2.5 | 1.5 |
| 5. Yellow pine sawdust | | 5.0 | 3.0 |
| 6. Pine Oil | | 1.0 | 0.6 |
| 7. Non-iodized sea salt | | 0.5 | 0.3 |
| Potable Water | | 68.45 | 41.07 |
| INOCULUM | Yeast *Saccharomyces Cerevisiae* | 0.05 | 0.03 |
| | *Bacillus Subtillis* spores | 10.0 | 6.0 |
| | *Bacillus Aglomerans* spores | 2.5 | 1.5 |
| | *Bacillus Megaterium* spores | 2.5 | 1.5 |
| Total | | 100% | 60 Kg |

Manufacturing Process for the Composition of Table 2

1. Take each of the ingredients 1 to 7 in the amounts referenced in table 2 and mix them in the same order in which they appear with 41.07 Kg of potable Water.

2. Heat the mixture from the previous step to a boil.

3. Allow the mixture to cool to room temperature.

4. Take a 500 ml sample from the top of the mixture obtained in step (3) above, and check to make sure that the sample does not contain any solid.

5. Add 0.03 kg (30.0 g) of yeast *Saccharomyces cerevisiae* (Fleischman brand) to the 500 ml sample taken in the previous step (4), mix slowly and manually until the yeast is fully incorporated.

6. Add the mixture from the previous step to the rest of the product referenced in step (3) and mix in gently for about 5 minutes 7. Store the product in a cool dry place, for eight days leaving some ventilation so gases from the fermentation process can escape. In the presence of the yeast the solids ferment anaerobically, the water also ferments and the top surface is fermented aerobically as well.

8. After completing the eight days of fermentation, the product is filtered using a filter housing fitted with a 40 micron mesh filter and a recirculating pump is used in order to remove biofilm that may be present in excess. The product is filtered several times.

9. Recirculate the product with the help of a diaphragm pump through a pipe exposed to electromagnetic fields (2-10,000 gauss) and then store in a tank for applying light stimuli. The electromagnetic field is adjusted so all the products from the fermentation are captured by the water molecules in the resulting product. Once everything is complexed with the water then the product is ready for the next step. A typical end point for this step is a reduction in the volatile content of the complex mixture.

10. The product is then treated with ultraviolet light of a frequency of 240-280 nm to give an aseptic product.

11. Add to the mixture of step (10) 6.0 Kg of *Bacillus Subtillis* spores and mix by hand for 5 minutes.

12. Add 1.5 Kg of *Bacillus Aglomerans* spores and mix by hand for 5 minutes.

13. Add 1.5 Kg of *Bacillus megaterium* spores and mix for 5 minutes.

14. Store the final product in containers of 4 and 20 kg.

For application to the field the product is further processed as follows:

1. 6 Liters of the product of Example 1 is further diluted with 30 liters of water and mixed manually and then allow mixing for about 15 minutes to start the latent phase.

2. Apply to the affected zones of the plant and to the insects. (Analysis of a sample of the product in a microbiological laboratory shows that there is a trillion of the three microorganisms added for every cubic centimeter of the product.

Example 2

Using the procedure of Example 1, the following product as shown in Table 3 is made.

TABLE 3

| | Ingredients | Percent by Wt (%) | Amount (Kg) |
|---|---|---|---|
| | Green Peas | 16.5 | 9.9 |
| | Potable Water | 68.45 | 41.07 |
| INOCULUM | Yeast *Saccharomyces Cerevisiae* | 0.05 | 0.03 |
| | *Bacillus Subtillis* spores | 10.0 | 6.0 |
| | *Bacillus Aglomerans* spores | 2.5 | 1.5 |
| | *Bacillus Megaterium* spores | 2.5 | 1.5 |
| | Total | 100% | 60 Kg |

Example 2A

Using the procedure of Example 1, the following product as shown in Table 3a is made.

TABLE 3a

| | Ingredients | Percent by Wt (%) | Amount (Kg) |
|---|---|---|---|
| | Red beans | 16.5 | 9.9 |
| | Potable Water | 68.45 | 41.07 |
| INOCULUM | Yeast *Saccharomyces Cerevisiae* | 0.05 | 0.03 |
| | *Bacillus Subtillis* spores | 10.0 | 6.0 |
| | *Bacillus Aglomerans* spores | 2.5 | 1.5 |
| | *Bacillus Megaterium* spores | 2.5 | 1.5 |
| | Total | 100% | 60 Kg |

Example 2B

Using the procedure of Example 1, the following product as shown in Table 3b is made.

TABLE 3b

| | Ingredients | Percent by Wt (%) | Amount (Kg) |
|---|---|---|---|
| | Yellow corn | 16.5 | 9.9 |
| | Potable Water | 68.45 | 41.07 |
| INOCULUM | Yeast *Saccharomyces Cerevisiae* | 0.05 | 0.03 |
| | *Bacillus Subtillis* spores | 10.0 | 6.0 |
| | *Bacillus Aglomerans* spores | 2.5 | 1.5 |
| | *Bacillus Megaterium* spores | 2.5 | 1.5 |
| | Total | 100% | 60 Kg |

Example 2C

Using the procedure of Example 1, the following product as shown in Table 3c is made.

TABLE 3c

| | Ingredients | Percent by Wt (%) | Amount (Kg) |
|---|---|---|---|
| | *Sorghum* | 16.5 | 9.9 |
| | Potable Water | 68.45 | 41.07 |
| INOCULUM | Yeast *Saccharomyces Cerevisiae* | 0.05 | 0.03 |
| | *Bacillus Subtillis* spores | 10.0 | 6.0 |
| | *Bacillus Aglomerans* spores | 2.5 | 1.5 |
| | *Bacillus Megaterium* spores | 2.5 | 1.5 |
| | Total | 100% | 60 Kg |

Example 2D

Using the procedure of Example 1, the following product as shown in Table 3d is made.

TABLE 3d

| | Ingredients | Percent by Wt (%) | Amount (Kg) |
|---|---|---|---|
| | Yellow pine sawdust | 16.5 | 9.9 |
| | Potable Water | 68.45 | 41.07 |
| INOCULUM | Yeast *Saccharomyces Cerevisiae* | 0.05 | 0.03 |
| | *Bacillus Subtillis* spores | 10.0 | 6.0 |
| | *Bacillus Aglomerans* spores | 2.5 | 1.5 |
| | *Bacillus Megaterium* spores | 2.5 | 1.5 |
| | Total | 100% | 60 Kg |

Example 3

Inorganic Composition as a Fermentation Additive

The inorganic component of the compositions is a mixture of naturally occurring minerals from the local rock formations Table 4 is a suitable composition.

TABLE 4

| Ingredients | Percent by Wt (%) | Quantity (Kg) |
|---|---|---|
| Phosphoric Minerals | 13.33 | 1.0 |
| Calcium containing Minerals | 66.67 | 5.0 |
| Silicic Minerals | 13.33 | 1.0 |
| Titanium and strontium containing minerals | 6.67 | 0.5 |
| Total Quantity of Product | 100% | 7.5 Kg |

Description of the Ingredients:

The ingredients of the inorganic formulations are obtained in manual form from different regions in Colombia which are rich in these substances.

The phosphoric minerals have low phosphoric concentration and are obtained in the Colombian region of the Huila from the piedmont rocks and in the flat part of the soil, these minerals are very soft and are collected in manual form by the natives of the region.

The calcium minerals are also obtained from the region of the piedmont plains in the western mountains of the Colombian andes and also it is a soft material and is mined manually.

The silicieous minerals are obtained manually from the south region of Colombia in Valle of the Cauca (Jamundi's Municipality) bordering the Cauca.

The titanium and strontium containing minerals are also mined manually in Palmira's city in Colombia (Valle region) near the airport, and in the cities of Tulua and Buga. This ingredients are characterized as having Calcium, Magnesium, Manganese among others and about an additional 70 elements of very low concentration.

Manufacturing Process:

1. The minerals are ground or milled and passed through a mesh sieve of 40, 60 or 80 microns, to produce very fine powders similar to the talc.

2. Each of the inorganic raw materials is added to a container of suitable capacity and mixed manually achieve a homogeneous appearance.

3. Place the mixture obtained in the previous step (2) in a tray to form a thin and homogeneous spreading mixture.

4. Expose the tray from the previous step using a lamp UV at wavelengths for aseptic treatment.

5. Store the product in plastic containers closed for future use according to need.

A typical analysis for the mineral of the invention reveal the following main components although clearly many minerals of this type have many trace elements present too and small variations in the mineral content will not affect the outcome of Applicants process. Those components are in Table 4a.

TABLE 4a

| Element | Chemical Symbol | Atomic # | ppm |
|---|---|---|---|
| Sodium | Na | 11 | 14.00 |
| Magnesium | Mg | 12 | 13000.00 |
| Aluminum | Al | 13 | 330.00 |
| Silicon | Si | 14 | Present as silicates |
| Phosphorus | P | 15 | 40.00 |
| Potassium | K | 19 | 21.00 |
| Calcium | Ca | 20 | 130000.00 |
| Titanium | Ti | 22 | 250.00 |
| Manganese | Mn | 25 | 27.00 |
| Iron | Fe | 26 | 810.00 |
| Cobalt | Co | 27 | 0.66 |
| Nickel | Ni | 28 | 1.70 |
| Copper | Cu | 29 | 0.84 |
| Zinc | Zn | 30 | 2.80 |
| Arsenic | As | 33 | 2.90 |
| Strontium | Sr | 38 | 660.00 |
| Barium | Ba | 56 | 17.00 |

Example 4

The ingredients of this formulation in Table 5 provide a composition that is useful for mixing with other products of the invention for enhancing their efficiency.

TABLE 5

| Ingredients | Percent by Wt (%) | Quantity (Kg) |
|---|---|---|
| Red Bean | 1.0 | 0.2 |
| Peas | 1.0 | 0.2 |
| White Rice | 5.0 | 1.0 |
| Yellow Corn | 1.0 | 0.2 |
| Example 3 Composition (Powder) | 0.05 | 0.01 |
| Non-iodized Salt | 0.05 | 0.01 |
| Potable Water | 91.85 | 18.37 |
| Inoculum *Bacillus Megaterium* | 0.05 | 0.05 |
| Total Quantity of Product | 100% | 20.0 Kg |

Manufacturing Process

1. Take the leguminous components (Red Bean 0.2 Kg and Peas 0.2 Kg (Oats can be used instead of peas without processing) and mix them together and crush them to reduce the size of the grains.

2. Add 0.4 Kg of potable water. Warm up to a first boil and then stop and let it cool until it reaches a temperature between 30 and 40° C.

3. In another container of suitable size, mix and crush the cereals (Rice 1.0 Kg and yellow corn 0.2 Kg). Add 1.2 Kg of water. Warm up to a first boil and then stop and let it cool until it reaches a temperature between 30 and 40° C.

4. Mix manually the mixtures obtained in steps 2 and 3 until reaching a homogeneous product.

5. Add 0.01 Kg of non-iodized salt and 0.01 Kg of the composition of Example 3 to the mixture obtained in the step 4 and mix manually to homogenize the product.

6. Inoculate the *Bacillus Megaterium* to the mixture of the previous step. Add additional potable water until the final weight is 20 kg.

7. Store the resulting mixture of step 6 in a cool and dry place, for eight days making sure there is enough space for the gases to escape from the process of fermentation.

8. After the eight days of storage the product is subjected to filtration using a filter provided with metallic mesh of 40 microns and then the liquid is recirculated with help of a pump in order to make sure the all the fine particles that could be present in the remaining biomass of the filtration could be removed.

9. The filetered product is further recirculated with the help of a diaphragm pump through a pipeline exposed to an electromagnetic field and then stored in a tank for application of UV light.

10. The product is the exposed to UV to create an aseptic product.

11. Store the product in the containers and date them as not usable after one year.

12. The product of step 11 can be used as inoculum for further preparations if desired i.e., a small sample (500 ml) of the lot by storing it between 1.0 and 5.0° C. The sample is good for about 60 days.

The potable waters used in the manufacturing process must be collected and allowed to remain in an open environment for two hours before using to guarantee the elimination of the chlorine that could be present in it. Afterwards, the water is subjected to recirculation in the presence of an electromagnetic field and UV light. The local water in Palmira, Valle, Colombia is ideal for this processes due to the fact it comes from natural high plateaus rivers or streams and has low pollution before being treated. This type of waters is used for all the formulations of the present invention.

Example 5

This product defined in Table 6 finds use as a fungicide.

TABLE 6

| Ingredients | Percent by Wt (%) | Quantity (Kg) |
|---|---|---|
| White Onion | 5.0 | 3.0 |
| Green Onion (Scalions) | 5.0 | 3.0 |
| Eucalyptus (Leaves And/Or Flowers) | 1.0 | 0.6 |
| Green Lemon Rinds | 1.0 | 0.6 |
| Nettle Leaves | 1.0 | 0.6 |
| Yucca Leaves | 1.0 | 0.6 |
| Nutmeg (Interior Part) | 1.0 | 0.6 |
| Composition of Example 3 | 1.0 | 0.6 |
| Potable Water | 83.95 | 50.37 |
| INOCULUM *Bacillus Subtillis* | 0.05 | 0.03 |
| Total Quantity of Product | 100% | 60 Kg |

Manufacturing Process

1. Take the quantities of each of the ingredients referenced in the table above (white onion, green onion, *eucalyptus* leaves or flowers, green lemon peels, nettle leaves, cassava leaves) and cut into small pieces, for the nutmeg discard the peel and take the inner part of the and reduce into small strips.

2. Mix all the above ingredients including example 3 powder with 19.2 Kg of potable Water (This amount corresponds to twice the weight of the solids in the formulation).

3. Heat the mixture from the previous step to a boil.

4. Allow the mixture to coot to room temperature and add the rest of water 31.17 kg 5. Add 0.03 kg (30.0 g) of *Bacillus Subtillis* to the preparation of the previous step (4), mix by hand until the total incorporation of the *Bacillus Subtillis*.

6. Store the product of step 5 in a cool dry place for five days leaving enough space for ventilation so you can dispose of gases from the fermentation process.

7. Filter the product after the five days of storage using a 40 micron mesh filter and recirculate the liquid using a pump in order to get all the biofilm which may be present in excess in the biomass.

8. Irradiate the product of step 7 using a UV tamp at a wavelength to provide an aseptic product.

9. Recirculate the product using a diaphragm pump through a pipe which is exposed to an electromagnetic field and store in a tank for applying UV light again if necessary.

10. Mix the Product of Example 4 with this product in a 1:1 ratio, in this case is 60 Kg with manual mixing for 5 minutes.

11. Store in containers suitable for 4 and 20 and 60 kg.

Product Application

The product is applied via a foliar spray pump at 1 or 2 liters per acre. The validity of the stored product is one year.

Example 6

This product defined in Table 7 is useful as a bactericide and fungicide.

TABLE 7

| Ingredients | Percent by Wt (%) | Quantity (Kg) |
|---|---|---|
| Green Onion (Scalions) | 5.0 | 3.0 |
| White Onions | 1.0 | 0.6 |
| Green Lemon Peel and Rinds | 1.0 | 0.6 |
| Nettle Leaves | 1.0 | 0.6 |
| Ruda Leaves | 1.0 | 0.6 |
| Wormwood Leaves (Absinthe) | 1.0 | 0.6 |
| Eucalyptus (Leaves And/Or Flowers) | 5.0 | 3.0 |
| Nutmeg (Interior Part) | 5.0 | 3.0 |
| Example 3 Composition | 1.0 | 0.6 |
| Potable Water | 78.95 | 47.37 |
| INOCULUM *Bacillus Aglomerans* | 0.05 | 0.03 |
| Total Quantity Product | 100% | 60 Kg |

Manufacturing Process

This product is made using the same procedure as in the previous Example except in step (2), the amount of water used is 25.2 Kg and in step (5) *Bacillus Aglomerans* is used instead of *Bacillus Subtillis.*

This product is also mixed with the product of example 4 in a 1:1 ratio, in this case is 60 Kg with manual mixing for 5 minutes.

Product Application

The product is applied via a foliar spray pump at 1 or 2 liters per acre. The validity of the stored product is one year.

Example 7

This product defined in Table 8 is useful to control and kill insects (insecticide).

TABLE 8

| Ingredients | Percent by Wt (%) | Quantity (Kg) |
|---|---|---|
| Green or Red peppers—Non-spicy | 5.0 | 3.0 |
| Peeled Garlic | 1.0 | 0.6 |
| Green Leaves Of *Citronella* | 1.0 | 0.6 |
| Red Beans | 1.0 | 0.6 |
| Mint Green Leaves | 1.0 | 0.6 |
| Nettle Leaves | 5.0 | 3.0 |
| Red Tomato Leaves And Fruit 50:50 | 1.0 | 0.6 |
| Ruda leaves | 5.0 | 3.0 |
| Example 3 Composition | 1.0 | 0.6 |
| Potable Water | 78.95 | 47.37 |
| INOCULUM *Bacillus Pseudomonas* | 0.05 | 0.03 |
| Total Quantity Product | 100% | 60 Kg |

Manufacturing Process

This product is made using the same procedure as in the previous Example except in step (5) *Bacillus Pseudomonas* is used instead of *Bacillus Aglomerans.*

This product is also mixed with the product of example 4 in a 1:1 ratio, in this case is 60 Kg with manual mixing for 5 minutes.

Product Application

The product is applied via a foliar spray pump at 1 or 2 liters per acre. The validity of the stored product is one year.

Example 8

This product defined in Table 9 is useful as a fungicide and bactericide.

TABLE 9

| Ingredients | Percent by Wt (%) | Quantity (Kg) |
|---|---|---|
| Raw Oats In Hull | 2.5 | 1.5 |
| Barley (Cereal) | 2.5 | 1.5 |
| Yucca Leaves | 1.0 | 0.6 |
| White Onion | 5.0 | 3.0 |
| Green Lemon Peel and Rinds | 5.0 | 3.0 |
| Green Leaves *Citronella* | 1.0 | 0.6 |
| Composition of Example 3 | 1.0 | 0.6 |
| Potable Water | 81.95 | 49.17 |
| INOCULUM *Bacillus Megaterium* | 0.05 | 0.03 |
| Total Quantity Product | 100% | 60 Kg |

Manufacturing Process

1. Take the oat hulls (1.5 Kg) and place them in a pressure cooker with steam outlet valve (Preferably Industrial Pressure Cooker Bellomatic of 7 liters capacity and high performance). Add 4.5 kg of hot potable water and cook for 15-20 minutes until the product consistency is soft.

2. Cook the barley like in step (1) until soft.

3. Mix the two products obtained in steps 1 and 2 to form a broth of Oats and Barley.

4. Add the rest of the ingredients which had been cut into small pieces.

5. Mix all the products of all the steps and add the composition of Example 3 with 15.6 Kg of potable water. (This amount corresponds to twice the weight of solids added in step 4).

6. Heat the mixture from the previous step to a boil and let cool to room temperature.

7. Add the oats and barley broth from step 3 to the mixture from step 6.

8. Add the remaining water 24.57 kg

9. Add 0.03 kg (30.0 g) of *Bacillus megaterium* to the preparation of the previous step (8), mix by hand until the total incorporation of *Bacillus megalerium.*

10. Resting Store product in a cool dry place for five days leaving little ventilation so you can dispose of gases from the fermentation process.

11. Filter the product after the five days of storage using a 40 micron mesh filter and recirculate the liquid using a pump in order to remove all the biofilm in the biomass.

12. Irradiate the product of step 7 using a UV lamp at a wavelength to provide an aseptic product.

13. Recirculate the product using a diaphragm pump through a pipe which is exposed to an electromagnetic field and store in a tank for applying UV light again if necessary.

14. Mix the Product of Example 4 with this product in a 1:1 ratio, in this case is 60 Kg with manual mixing for 5 minutes.

15. Store in containers suitable for 4 and 20 and 60 kg

Product Application

The product is applied via a foliar spray pump at 1 or 2 liters per acre. The validity of the stored product is one year.

Example 9

This product defined in Table 10 is used as fertilizer on phytoplankton.

TABLE 10

| | Ingredients | Percent by Wt (%) | Quantity (Kg) |
|---|---|---|---|
| | Soya (Leaves And Fruits 50:50) | 5.0 | 3.0 |
| | Celery (Leaves And Branches) | 2.0 | 1.2 |
| | Basil(Leaves) | 2.0 | 1.2 |
| | Composition of Example 3 | 1.0 | 0.6 |
| | Potable Water | 79.95 | 47.97 |
| INOCULUM | Yeast *Saccharomyces cerevisiae* | 10.0 | 6.0 |
| | *Bacillus megaterium* | 0.05 | 0.03 |
| | Total Quantity of Product | 100% | 60 Kg |

Manufacturing Process

1. Take the quantities of each of the ingredients referenced in the table above (Soya (Half and Half Fruit leaves), celery (leaves and branches), Basil (leaves)) and cut into small pieces.

2. Mix all the blend of step (1) including composition of Example 3 (Powder) with 12.0 Kg of Potable Water (This amount corresponds to twice the weight of the solids in the formulation).

3. Heat the mixture from the previous step to a boil.

4. Allow the mixture to cool to room temperature and add the rest of water 35.97 kg 5. Take a sample of approximately 2 liters of the top of the mixture obtained in the previous step (4), check that the sample does not contain any solid, Add 6.0 kg of yeast *Saccharomyces cerevisiae* (Fleischman Brand) to the sample taken, slowly and mix by hand until the total incorporation of yeast.

6. Add the mixture from the previous step to the rest of the product referenced in step (4) and mix in gently for 5 minutes.

7. Take a sample of approximately 0.5 liters of the top of the mixture obtained in the previous step (4), check that the sample does not contain airy solid. Add 0.03 Kg (30.0 g) of *Bacillus megaterium* to the sample taken, slowly and mix by hand until the total incorporation of *B. Megaterium.*

8. Add the mixture from the previous step to the rest of the product referenced in step (4) and mix in gently for 5 minutes.

9. Store the resulting mix of step (8) in a cool dry place for five days leaving enough room for the gases from the fermentation process to escape.

10. Filter the product after the five days of storage using a 40 micron mesh filter and recirculate the liquid using a pump in order to get all the biofilm which may be present in excess in the biomass.

11. Irradiate the product of step 7 using a UV lamp at a wavelength to provide an aseptic product.

12. Recirculate the product using a diaphragm pump through a pipe which is exposed to an electromagnetic field and store in a tank for applying UV light again if necessary.

13. Mix the Product of Example 4 with this product in a 1:1 ratio, in this case is 60 Kg with manual mixing for 5 minutes.

14. Store in containers of 4 and 20 and 60 kg

Product Application

1. Apply 1.5 liters of product water per acre of lake culture, the product has a shelf life of one year.

Example 10

This product defined in Table 11 is useful as a fertilizer.

TABLE 11

| | Ingredients | Percent by Wt (%) | Quantity (Kg) |
|---|---|---|---|
| | Orégano (Leaves) | 5.0 | 3.0 |
| | Soya (Leaves And Fruits 50:50) | 2.5 | 1.5 |
| | Celery (Leaves And Branches) | 2.5 | 1.5 |
| | Basil (Leaves) | 5.0 | 3.0 |
| | Salitre (Guano)(2) | 20.0 | 12.0 |
| | Composition of Example 3 | 1.0 | 0.6 |
| | Potable Water | 63.95 | 38.37 |
| INOCULUM | *Bacillus megaterium* | 0.05 | 0.03 |
| | Total Quantity Product | 100% | 60 Kg |

Manufacturing Process

1. Take the quantities of each of the ingredients referenced in the table above (Oregano Leaves, Leaves and Fruits of Soya in 50:50, Leaves and Branches and celery leaves, basil leaves, Salitre (Guano) (2)) and cut into small pieces or shred them if necessary.

2. Mix all above ingredients including the composition of Example 3 (Powder) with 21.6 Kg of Potable Water (This amount of water corresponds to the weight of the solids in the formulation).

3. Heat the mixture from the previous step to a boil.

4. Allow mixture to cool to room temperature and add the rest of water 16.77 kg

5. Add 0.03 kg (30.0 g) of *Bacillus megaterium* to the preparation of the previous step (4), and mix by hand until the total incorporation of the *Bacillus megaterium.*

6. Store the product of step (5) in a cool dry place for five days leaving enough space so the gases from the fermentation process can escape.

7. Filter the product after the five days of storage using a 40 micron mesh filter and recirculate the liquid using a pump in order to get all the biofilm which may be present in excess in the biomass.

8. Irradiate the product of step 7 using a UV lamp at a wavelength to provide an aseptic product.

9. Recirculate the product using a diaphragm pump through a pipe which is exposed to an electromagnetic field and store in a tank for applying UV light again if necessary.

10. Mix the Product of Example 4 with this product in a 1:1 ratio, in this case is 60 Kg with manual mixing for 5 minutes.

11. Store in gallons of 4 and 20 and 60 kg

Product Application

The product is applied via foliar spray pump at 1 or 2 liters per acre. The product has shelf life of one year.

The Guano component (2) is the material formed from coastal bird droppings. It is a very valuable material, due to its application in fertilizers and explosives. These characteristics are due to the guano high concentrations of phosphorus and nitrogen.

Chemically guano comprises ammonium nitrate together with uric acid, phosphoric acid, oxalic acid and carbonic addition salts and other impurities.

Example 11

The product defined in Table 12 is used as fertilizer, and it helps with the soil nitrogen fixation.

TABLE 12

| | Ingredients | Percent by Wt (%) | Quantity (Kg) |
|---|---|---|---|
| | Mata-Raton (Leaves) (*Gliricidia Sepium* (Jacquin)) | 2.5 | 1.5 |
| | Red Bean | 2.5 | 1.5 |
| | Yellow Corn | 5.0 | 3.0 |
| | White Rice | 5.0 | 3.0 |
| | Basil Oil | 1.0 | 0.6 |
| | Composition of Example 3 | 1.0 | 0.6 |
| | Non-iodized Salt | 0.5 | 0.3 |
| | Potable Water | 67.45 | 40.47 |
| INOCULUM | Yeast *Saccharomyces cerevisiae* | 0.05 | 0.03 |
| | *Azotobacter* | 15.0 | 9.0 |
| | Total Quantity Product | 100% | 60 Kg |

Manufacturing Process

1. Take the quantities of each of the ingredients referenced in the table above (mata-raton Sheets, Yellow Corn, White Rice, Basil Oil, and non-iodized sea salt) and cut into small pieces or shred them in case it applies.

2. Mix all above step ingredients including the composition of Example 3 (Pwder) with 21.0 Kg of Potable Water (This amount of water corresponds to twice the weight of the solids irr the formulation).

3. Heat the mixture from the previous step to a boil.

4. Allow mixture to cool to room temperature and add the rest of water 19.47 kg.

5. Take a sample of approximately 500 ml of the top of the mixture obtained in the previous step (4), check that the sample does not contain any solids.

6. Add 0.03 kg (30.0 g) of yeast *Saccharomyces cerevisiae* (Fleischman Brand) to the sample taken in the previous step (5) and mix by hand until the total incorporation of all the yeast.

Add the mixture from the previous step to the rest of the product, referenced in step (4) and mix in gently for about 5 minutes.

8. Store the product in a cool dry place, for eight days leaving some space for the gases from the fermentation process to escape.

9. Filter the product after the five days of storage using a 40 micron mesh filter and recirculate the liquid using a pump in order to get all the biofilm which may be present in excess in the biomass.

10. Irradiate the product of step 9 using a UV lamp at a wavelength to provide an aseptic product.

11. Recirculate the product using a diaphragm pump through a pipe which is exposed to an electromagnetic field and store in a tank for applying ITV light again if necessary.

12. Add to the mixture of step (11), 9.0 Kg of the microorganism *Azotobacter* and mix by hand for 0.5 minutes.

13. Store in containers of 4 and 20 kg.

Example 12

This product defined in Table 13 is useful for wastewater treatment, decontamination of water and soil with traces of hydrocarbons and organophosphates.

TABLE 13

| | Ingredients | Percent by Wt (%) | Quantity (Kg) |
|---|---|---|---|
| | Garbanzo | 2.5 | 1.5 |
| | Lentils | 2.5 | 1.5 |
| | Barley | 5.0 | 3.0 |
| | Oat Hulls | 5.0 | 3.0 |
| | Citric Oil | 1.0 | 0.6 |
| | Composition of Example 3 | 1.0 | 0.6 |
| | Non-iodized Salt | 0.5 | 0.3 |
| | Potable Water | 67.45 | 40.47 |
| INOCULUM | Yeast *Saccharomyces cerevisiae* | 0.05 | 0.03 |
| | *Bacillus megaterium* | 10.0 | 6.0 |
| | *Bacillus subtillis* | 2.5 | 1.5 |
| | *Bacillus lincheniformis* | 2.5 | 1.5 |
| | Total Quantity of Product | 100% | 60 Kg |

Manufacturing Process

1. Take the quantities of each of the ingredients referenced in the table above (Garhanzo, Lentil, Barley, Oats, Citrus Oil, Sea. Salt) and shred them into smaller pieces.

2. Mix all above ingredients including the composition of Example 3 (Powder) with 21.0 Kg of Potable Water (This amount of water corresponds to twice the weight of the solids in the formulation).

3. Heat the mixture from the previous step to a boil.

4. Allow mixture to cool to room temperature and add the rest of water 19.47 kg

5. Take a sample of approximately 500 mL of the top of the mixture obtained in the previous step (4), and check that the sample does not contain any solid.

6. Add 0.03 kg (30.0 g) of yeast *Saccharomyces cerevisiae* (Fleischman Brand) to the sample taken in the previous step (5) and mix by hand until all the yeast is incorporated.

7. Add the mixture from the previous step to the rest of the product referenced in step (4) and mix in gently for about 5 minutes 8. Store product in a cool dry place, for eight days leaving some space for the gases from the fermentation process to escape.

9. Fitter the product after the eight days of storage using a 40 micron mesh filter and recirculate the liquid using a pump in order to get all the biofilm which may be present in excess in the biomass.

10. irradiate the product of step 9 using a UV lamp at a wavelength to provide an aseptic product.

11. Recirculate the product using a diaphragm pump through a pipe which is exposed to an electromagnetic field and store in a tank for applying UV light again if necessary.

12. Add to the mixture of step (11) 6.0 Kg of *Bacillus megaterium* and mix by hand for 5 minutes.

13. Add 1.5 Kg of *Bacillus Subtillis* and mix by hand for 5 minutes.

14. Stir in the 1.5 Kg of *Bacillus Lincheniformis* and mix for 5 minutes.

15. Store in containers of 4 and 20 kg.

Example 13

This product defined in Table 14 is used as a degreaser and in composting processes, accelerates the degradation of organic matter and degrading organic compounds.

TABLE 14

| Ingredients | Percent by Wt. (%) | Quantity (Kg) |
|---|---|---|
| Garbanzo | 5.0 | 3.0 |
| Lentils | 5.0 | 3.0 |
| Barley | 2.5 | 1.5 |
| Oat Hulls | 2.5 | 1.5 |
| Citric Oil | 1.0 | 0.6 |
| Composition of Example 3 | 1.0 | 0.6 |
| Sea Salt (Non Iodine) | 0.5 | 0.3 |
| Potable Water | 67.45 | 40.47 |
| INOCULUM Yeast *Saccharomyces cerevisiae* | 0.05 | 0.03 |
| *Bacillus megaterium* | 10.0 | 6.0 |
| *Bacillus pseudomonas* | 5.0 | 3.0 |
| Total Quantity of Product | 100% | 60 Kg |

Manufacturing Process

Take the quantities of each of the ingredients referenced in the table above (Garhanzo, Lentil, Barley, Oats, Citrus Oil, non-iodized Sea. Salt) and shred them into smaller pieces.

2. Mix all of above ingredients including the composition of Example 3 (Powder) with 21.0 Kg of Potable Water (This amount of water corresponds to twice the weight of the solids in the formulation).

3. Heat the mixture from the previous step to a boil.

4. Allow the mixture to cool to room temperature and add the rest of water 19.47 kg.

5. Take a sample of approximately 500 ml from the top of the mixture obtained in the previous step (4), and check that the sample does not contain any solid.

6. Add 0.03 kg (30.0 g) of yeast *Saccharomyces cerevisiae* (Fleischman Brand) to the sample taken in the previous step (5) and slowly mix by hand until all of the yeast is incorporated.

7. Add the mixture from the previous step to the rest of the product referenced in step (4) and mix in gently for about 5 minutes.

8. Store the product in a cool dry place, for eight days leaving enough space so the gases from the fermentation process can escape.

9. Filter the product after the eight days of storage using a 40 micron mesh filter and recirculate the liquid using a pump in order to get all the biofilm which may be present in excess in the biomass.

10. Irradiate the product of step 9 using a UV lamp at a wavelength to provide an aseptic product.

11. Recirculate the product using a diaphragm pump through a pipe which is exposed to an electromagnetic field and store in a tank for applying UV ht again if necessary.

12. Add to the mixture of step (11) 6.0 Kg of *Bacillus megaterium* and mix by hand for 5 minutes.

13. Add the *Bacillus Pseudomonas* and mix by hand for 5 minutes.

14. Store in containers of 4 and 20 kg.

Example 14

This product defined in Table 15 is useful for remineralization of soils and crops, and increases soil biodynamic production.

TABLE 15

| Ingredients | Percent by Wt. (%) | Quantity (Kg) |
|---|---|---|
| Phosphoric Minerals | 29.40 | 5.0 |
| Calcium Minerals | 58.82 | 10.0 |
| Siliceous Minerals | 5.89 | 1.0 |
| Titanium and strontium containing minerals | 5.89 | 1.0 |
| Total Quantity of Product | 100% | 17.0 Kg |

Manufacturing Process

1. Take all the raw materials and pass them through a special fine 60 micron sieve, until each of the raw materials have the appearance of very fine powder (Similar to talc).

2. Add each of the raw materials in a container of suitable capacity and perform hand mixing until the product is homogenous in appearance.

3. Place the mixture obtained in the previous step (2) in a tray and spread it to form a thin, even layer.

4. Expose the product from step (3) to UV light.

5. Store in sealed plastic containers for use as needed.

Example 15

This product defined in Table 16 is useful in sewage treatment systems, aerobic and facultative, oxidation ponds and soil contamination.

TABLE 16

| Ingredients | Percent by Wt (%) | Quantity (Kg) |
|---|---|---|
| Phosphoric Minerals | 11.76 | 1.0 |
| Calcium Minerals | 58.82 | 5.0 |
| Siliceous Minerals | 23.52 | 2.0 |
| Titanium and strontium containing minerals | 5.90 | 0.5 |
| Total Quantity of Product | 100% | 8.5 Kg |

Manufacturing Process

Take all the raw materials and pass them through a special fine 80 micron sieve, until each of the raw materials have the appearance of very fine powder (Similar to talc).

2. Add each of the raw materials in a container of suitable capacity and perform hand mixing until the product is homogenous in appearance.

3. Place the mixture obtained in the previous step (2) in a tray and spread it to form a thin, even layer.

4. Expose the product of the last step to UV light. This step is done for safety since the product is characterized by having good stability and is not prone to contamination whatsoever.

5. Store in sealed plastic containers for use as needed.

Example 16

The product defined in Table 17 is used in aquaculture activities and can be used in conjunction with the product of Example 9 to get best results.

TABLE 17

| Ingredients | Percent by Wt (%) | Quantity (Kg) |
|---|---|---|
| Phosphoric Minerals | 8.0 | 1.0 |
| Calcium Minerals | 80.0 | 10.0 |
| Siliceous Minerals | 8.0 | 1.0 |

TABLE 17-continued

| Ingredients | Percent by Wt (%) | Quantity (Kg) |
|---|---|---|
| Titanium and strontium containing minerals | 4.0 | 0.5 |
| Total Quantity of Product | 100% | 12.5 Kg |

Manufacturing Process

1. Take all the raw materials and pass them through a special fine 80 micron sieve, until each of the raw materials have the appearance of very fine powder (Similar to talc).
2. Add each of the raw materials in a container of suitable capacity and perform hand mixing until the product is homogenous in appearance.
3. Place the mixture obtained in the previous step (2) in a tray and spread it to form a thin, even layer.
4. Expose the product of the last step to UV light. This step is done for safety since the product is characterized by having good stability and is not prone to contamination whatsoever.
5. Store in sealed plastic containers for use as needed.

Example 17

The product defined in Table 18 is used in ethanol production and can be used in yeast propagation.

TABLE 18

| Ingredients | Percent by Wt (%) | Quantity (Kg) |
|---|---|---|
| White Rice | 10.0 | 6.0 |
| Brown Rice | 10.0 | 6.0 |
| Salitre/manure (Guano)* | 40.0 | 24.0 |
| Composition of Example 3 | 0.6 | 0.36 |
| Potable Water | 39.30 | 23.58 |
| INOCULUM Saccharomyces cerevisiae | 0.10 | 0.06 |
| Total Quantity Product | 100% | 60 Kg |

*The dried excrement of fish-eating sea birds, deposited in rocky coastal regions of South America: contains the urates, oxalates, and phosphates of ammonium and calcium; used as a fertilizer or any similar but artificial fertilizer.

Manufacturing Process

1. Take the quantities of each ingredient on the table except the yeast and the saltpeter/manure and add them to half the volume of the water amount outlined on the table and then heat the mixture to a boil.
2. Allow the mixture to cool to room temperature and then add the rest of the potable water.
3. Manually add the yeast mix.
4. Let the entire resulting mix stand in a cool dry place for five days leaving some ventilation space to dispose of gases from the fermentation process.
5. Filter the fermented products after five days of storage using a filter fitted with 40 micron mesh and recirculating the fluid using a pump to remove insolubles that may be present in excess.
6. Mix with saltpeter/manure and blend until homogenized.
7. Expose the product to UV light to create an aseptic product.
8. Recirculate the product with the help of a diaphragm pump through a pipe exposed to an electromagnetic field and store in a tank to apply further light stimuli.
9. Add the product of Example 4 to the mixture in 2:1 ratio in this case is 30 kg manually and mix for 5 minutes.
10. Store in gallons of 4 and 20 and 60 kg Product Application The product is used in fermentation processes. It is recommended that the application be at a level of 20 ppm relative to the total fermentation mash.

Example 18

The product of this example in Table 19 is used as a growth stimulant and ripener.

TABLE 19

| Ingredients | Percent by Wt (%) | Quantity (Kg) |
|---|---|---|
| Horse Tail Fern (*Equisetaceae*) | 10.0 | 6.0 |
| Plantain leaves | 10.0 | 6.0 |
| White Onion | 2.0 | 1.20 |
| Nettle leaves | 2.0 | 1.20 |
| Eucaliptus leaves and flowers | 2.0 | 1.20 |
| Composition of Example 3 | 2.0 | 1.20 |
| Potable Water | 71.49 | 43.14 |
| INOCULUM Saccharomyces cerevisiae | 0.10 | 0.06 |
| Total Quantity Product | 100% | 60 Kg |

Manufacturing Process

1. Take the amounts of each of the ingredients in about 50% of the required water (except the yeast) and heat the mixture to a boil.
2. Allow mixture to cool to room temperature and add the rest (50%) of potable water.
3. Manually add the yeast mix.
4. Store the resulting product in a cool dry place for five days leaving some room for ventilation so gases can escape from the fermentation process.
5. Filter the resulting product of step 4, using a filter housing fitted with 40 micron mesh and recirculate the filtrates using a pump in order to all the biofilm which may be present in excess.
6. Make an aseptic product by applying UV light.
7. Recirculate the product with the help of a diaphragm pump through a pipe provided with electromagnetic fields and stored in a tank for applying light stimuli.
8. Mix with the product of example 4, adding to the mixture in a 1:1 ratio, in this case is 60 Kg and manually mixing for 5 minutes.
9. Store in gallons of 4, 20 and 60 kg size.

Product Application

Apply 1-2 liters per acre at flowering to stimulate floral reproduction and prevent abortions.

Apply 1-2 liters per acre while in the stages of fruit and grain production to increase size and weight.

In sugar cane ripening apply 1 to 2 liters per acre 90 days before cutting to increase sucrose concentration and number of resproutings after cutting.

The yeast used is *Saccharomyces cerevisiae*. It is obtained commercially as baker's yeast.

Example 19

This product defined in Table 20 aids in the stabilization of stomach pH levels in order to prevent creation of stomach acids, which disrupt the digestive flow, preventing the erosion of the stomach mucus membrane and reducing the incidence of ulcers, gastritis, and reducing conditions which have been linked to stomach cancer. Reduces the number of the *Helicobacter pilori* bacteria in the intestinal track by trapping and elimination through the digestive tract and creating conditions for the increase of beneficial intestinal flora.

TABLE 20

| Ingredients | Percent by Wt (%) | Quantity (Kg) |
|---|---|---|
| Calcium Minerals | 80.0 | 10.0 |
| Siliceous Minerals | 20.0 | 2.50 |
| Total Quantity of Product | 100% | 12.5 Kg |

Manufacturing Process

1. Take all the raw materials and pass them through a fine sieve of 40 microns, to ensure that each of the raw materials have the appearance of very fine powder (Similar to talc).
2. Add each material in a container of adequate capacity and perform manual mixing until the product has a homogeneous appearance.
3. Place the mixture obtained in step (2) in a tray and spread it into a thin, even layer.
4. Expose the product of step (3) to UV treatment as in the previous examples. This step is done for safety as the product is characterized by having good stability and is not prone to contamination of any kind.
5. Store in closed plastic containers for use as needed.

Example 20

Use of the Product of Example 1 to Treat Stable Flies (*Stomoxys calcitrans*)

Costa Rica has had a very significant increase in the areas dedicated to the production of pineapple for export. The risks in production and plant protection becomes a priority as the level of safety of the fruit also becomes important as international customers impose new regulations and/or certifications to ensure that the Permitted Maximum Residue Limits are met by the country Farming Practice and Processes. This trend will not change and therefore good farming practices must venture into the pest control products different from those based on chemicals and replace them with organic products that do not generate environmental problems and are safe for use from the point of view of human health.

Application to Plant Parts

The composition of the present invention can be applied to plant parts as a dry material or as a wet formulation. As a dry material, the composition can be applied directly to the plant parts to be protected, for example leaves. The dry material can also be applied to the whole plant, fruits, and the like by dusting. The wet formulation can be applied by spraying onto the plant parts to be protected, or the plant parts can be dipped in the wet formulation, for example by dipping them.

Of course the soil where the pineapple plant is grown can also be treated with the product of Example 1.

Procedure for Spraying Product of Example 1

1. The water used for activation of the microorganisms present in the Example 1 product must be conditioned to a pH between 5 and 6, by using lemon juice was and monitored with a pH meter to adjust the pH to the required value.
2. The microorganisms in the product of Example 1 were activated in a mixture with non-chlorinated water in a ratio of 1:5, i.e., one liter product of Example 1 with 5 liters unchlorinated water. Stir and let stand for 15 minutes.

3. Once the activation is completed the product is placed in a Spray Boom tank and additional water was added to have product for application to an acre.
4. The product was applied at the rate of a dose of 13 liters/acre. Prior to application a calibration was done. The second application was done at a dose of 7 liters/acre.
5. Sample populations per square meter were chosen randomly in the experimental acreage.
6. The first sampling took place five days after the first application. The second sampling occurred four days after the second application.

The results of the treatment are summarized in the tables below:

| After 5 days | | | |
|---|---|---|---|
| | Population per square meter | | |
| | Eggs | larvae | Pupae |
| Product of Example 1 | 0 | 0.5 | 0.5 |
| Control | 0 | 7.5 | 0 |

| After 4 days | | | |
|---|---|---|---|
| | Population per square meter | | |
| | Eggs | larvae | Pupae |
| Product of Example 1 | 0 | 0.25 | 0 |
| Control | 0 | 1.50 | 0 |

1. Odors in the treated plot with Example Bioblast when the samples were being made were not perceived i.e., fermentation or putrefaction, while with the control the odor was very perceptible.
2. As you can see in the table of results above, treatment with the formulation of Example 1 results in striking reduction of the larvae and pupae when compared to the control.
3. Within five days after the first application, the plot treated with the product of Example 1 had 1500% less larvae when compared with the control.
4. Four days after the second application, the plot treated with product of Example 1 had 600% less larvae when compared to the control.

Therefore, it is clear that the product of Example 1 is very effective for controlling stable flies, *Stomoxys calcitrans*.

Example 21

Use of the Product of Example 1 to Treat Moko (*Ralstonia solanacearum*)

*Ralstonia solanacearum* is a pathogen of worldwide distribution, infecting about 200 species of plants, including Musa and gingiberaceas and resposnsible for causing the disease Moko". The organism is a Gram-negative bacterium. It has been studied by extensively by plant pathologists and used by molecular biologists as a model to explain the genetic mechanisms that govern pathogenicity in plants. The bacteria can survive in the soil, water and plant debris, plus it spreads rapidly and the established controls have proved inefficient in its eradication because of the versatility of the pathogen. The product of Example 1 is particularly useful in reducing the aggressiveness of *Ralstonia solanacearum*.

Moko on Heliconias caused by *R. solanacearum* is a very versatile free-living organism. The classification system of the bacteria makeup is governed by host range, pathogenicity, geographic distribution and genetic differences.

The bacteria can be revived even after a sleep state and persist in the infection of many plant species. In water the bacteria can survive in unfavorable conditions, achieves low latency can withstand temperatures critically and recover in a short time interval between 18° C. and 25° C. Light is an important factor in the distribution of colonies, soils with *R. solanacearum* can coexist with other species of bacteria, fungi and higher organisms and in some regions the presence of agricultural activity causes an imbalance in favor of harmful organisms such as *Erwinia* sp, *Fusarium* sp, *Phytohpthora Rizotocnia* sp and even nematodes.

The bacteria can spread from plant wounds, runoff, splash, infected seeds, insects and tools. For this disease nothing in the prior art is efficacious, although biological control and organic leachate extract in cultivated areas has provided interesting results in decreasing the incidence of *R. solanacearum.*

For application of the product of Example 1, we used two cans of 200 liters each. In a 200 liter container there were added 4 liters of Example 1 product to 20 liters of water, then allowed to stand for 15 minutes and then diluted further with 176 liters of water.

The other container is made the same way. To the sprayer was added 10 liters of water and 10 liters of the product of Example. The dosage per plant is 300 ml per plant. For the bio-activation the product of Example 1 is in a pre mix ratio of 1 liter of product with 5 liters of water, stir and let stand for 15 minutes. These products are applied without any mixing with others.

The field trial was conducted over a three month period on four lots of heliconias with different numbers of plants and different ages. The products can be applied to the soil or the application can be made by foliar application. The first two applications were made at an interval of two weeks, the other three applications were made at ten day intervals.

At 8 days after the first application was made, visual observations were made in the field to determine the behavior of plants such products. Samples from each batch of plants with or without symptoms of moko (*Ralstonia solanacearum*) were taken to the local Plant Health Diagnostic Laboratory to check for the presence of this bacterium in plants.

In the samples collected from each batch we performed a cross-sectional analysis to see if they had symptoms of bacteria in the rhizome or pseudostem.

One batch had 198 plants, 1 months crop age, growing area 1485.37 $m^2$. Of the 198 plants 185 were healthy plants, and 13 were diseased plants (7%). This batch was the most tolerant to this bacteria.

Example 22

Palm oil producing palms that have bud rot are treated with the product of Examples 1, 5, 6 or 8. FIG. 1 shows an untreated palm spear having bud rot. FIG. 2 shows a treated palm spear which is free of bud rot after treatment.

Example 23

A waste water pond containing waste from a pineapple processing plant is treated with the products of Example 1 (4.25 liters per day diluted with non-chlorinated water at a ration of 1:5), Example 12 (1 liter per day diluted with non-chlorinated water at a ration of 1:5), and Example 13 (2 liters per day diluted with non-chlorinated water at a ratio of 1:5).

The results of the treatment are summarized in table 21 below.

TABLE 21

| | Unit | Reference value | Before Treatment | After 4 months Treatment | % Removal |
|---|---|---|---|---|---|
| COD | mg/L | 400 | 9,637 | 990 | 89.73 |
| BOD | mg/L | 150 | 3,075 | 317 | 89.69 |
| Suspended Solids | mg/L | 150 | 150 | 184 | 38.67 |
| Sediment | ml/L | 1 | 1.30 | 0.10 | 92.31 |
| Oil and Grease | mg/L | 30 | 20.50 | 9.00 | 56.10 |
| pH | | 5-9 | 6.50 | 6.10 | 6.15 |
| Temperature | | <40 | 30.30 | 28.50 | 5.94 |
| SAAM* | mg/L | 5 | 12.05 | 4.47 | 62.90 |
| Residual Chlorine | mg/L | 1 | ND | ND | Negative |

*Methylene Blue active substances

Example 24

Use of the Composition of Example 18 for Stimulating Growth/Ripening of Sugar Cane.

The composition of Example 18 is applied to a sugar cane plantation at the rate of 1-2 liters per acre (or 13.5 fluid ounces per acre) 3 months prior to harvesting. The results of this example are summarized in FIGS. 4-7 and compared to glyphosate (control) which in the sugar cane industry is also used as a ripener.

The composition of Example 18 may be applied several times a year too.

Example 25

Use of the Products of Examples 9 and 16 in Fish Ponds.

Four fish each were collected from two fish ponds. One pond was treated with the products of Examples 9 and 16 and the other pond was the control. The fish were carried in plastic bags to the laboratory to examine their health status.

The fish were placed in separate buckets and then proceeded to the analysis of their health. The fish were first externally evaluated to determine the presence or absence of lesions in the skin, eyes and fins. Subsequently the fish were killed and opened to inspect the internal organs. The organs were removed for analysis individually. In the case of the gills, the stomach and intestine, they were dissected to determine differences between the control and treated ponds.

Of the total inspections, only differences in stomach contents were detected. The fish from the treated pond along with newly ingested pellets, had lots of greenish color stuff similar to microalgae. In the case of the control, two of the fish only had a tiny presence of microalgae while tow of them had none.

For the gills no differences were observed, they all had the same color and just as with feces, no visual differences were found.

Example 26

Rice plantations that have been infected with the rice tarsonemid mite and the bacterium *B. glumae*. are treated with the product of Examples 1, 5, 6, 7 or 8. The rice plant shows significant improvement in not showing empty head or grain sterility The uses of all the products of the invention described in the above examples are summarized in Table 22 below:

TABLE 22

| Examples | Mode of Action | Applications |
| --- | --- | --- |
| Example 1 | Soil Innoculation - Microorganisms | Palm (PC), Banana (Moko), Stable Fly, Cacao (*Monelia* & *Rosellinia*), Flowers (pathogen complex), Rice, Palm (PC) |
| Example 1 | Foliar application - Microorganisms | Palm (PC) |
| Example 1 | Organic material digester | Residual Waters - Odors and Vectors + Hydrocarbon and Chemical cleanup |
| Example 11 | Biological Fixation of Nitrogen - fertilizer | Palm (Fert & PC), Banana (Fert. & Moko), Sugar Cane |
| Example 11 | Biodigestor—Nitrogen compounds | Residual waters |
| Example 13 | Suppresive Soils - Innoculation Microorganisms | Accompanies Example Bioblast—creates hostile environment in soils for pathogen growth |
| Example 13 | Digester of Organic Matter | Residual Waters |
| Example 12 | Digester Hidrocarbons and Toxic Elements | Hydrocarbon and Chemical Clean-up Soils |
| Examples 3, 14, 15, 16 | Biocinetic inducer soils, substrates and waters | Residual waters, wetlands & Hydrocarbon and chemical cleanup |
| Example 10 | Organic Fertilizer - NPK | Palm (Fert. & PC), Banana (Fert & Moko), Sugar Cane (Fert) |
| Example 14 | Biopotentiation - soils and plants | Palm (fert & PC), Banana (fert & Moko), Sugar cane (fert.) |
| Example 7 | Insect resistance inducer | Palm (PC) |
| Example 5 | Fungus resistance inducer | Palm (PC), Banana (Moko) |
| Example 6 | Resistance inducer against complexes | Palm (PC), Banana (Moko) |
| Example 8 | Control of Complexes | Palm (PC), Banana (Moko) |
| Example 9 | Fertilizer phytoplankton | Proven product in various locations |
| Example 16 | Biopotentiation-origin Mineral | Proven product in various locations |
| Example 19 | Gastrointestinal biocinetic inducer | Human gastrointestinal applications |
| Example 17 | Organic fertilizer for fermentation process (alcohols, lactic, vinasse, etc) | alcohol, lactic products |
| Example 17 | Organic fertilizer for protein production and acid fermentations in lactic prods. | |
| Example 18 | Organic ripener | sugar cane, coffee, |
| Star Fuel | Fuel Additive, Petroleum liquefaction | increase in caloric content reduction of viscocity |
| Example 10 | Nitrogen Compounds Biodigestor | Residual waters |

The content of all references cited in the instant specification and all cited references in each of those references are incorporated in their entirety by reference herein as if those references were denoted in the text While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is claimed is:

1. A biopesticidal composition for agricultural use comprising a mixture of: (a) a first product of fermenting in water a mixture of one of more natural products selected from the group consisting of red beans, peas, white rice and yellow corn with *Saccharomyces cerevisiae*, and (b) a second product containing non-iodized salt, water, *Bacillus megaterium*, and 0.05 to 2.0% by weight of a mixture of inorganic minerals comprising phosphorus, calcium, silicon, titanium, and strontium.

2. The biopesticidal composition of claim 1, further comprising one or more natural products selected from the group consisting of white onions, green onions, scalions, *Eucalyptus* leaves and/or flowers, green lemon peels and rinds, nettle leaves, *Yucca* leaves, and interior part of nutmeg, and an inoculum comprising *Bacillus subtilis*.

3. The biopesticidal composition of claim 1, further comprising one or more natural products selected from the group consisting of green onion, scalions, white onions, green lemon peel and rinds, nettle leaves, ruda leaves, wormwood leaves, leaves and/or flowers of *Eucalyptus*, and interior part of nutmeg, and an inoculum comprising *Bacillus agglomerans*.

4. The biopesticidal composition of claim 1, further comprising one or more natural products selected from the group consisting of green or non-spicy red peppers, peeled garlic, green leaves of citronella, mint green leaves, nettle leaves, red tomato leaves and fruit, and ruda leaves, and an inoculum comprising *Pseudomonas*.

5. The biopesticidal composition of claim 1, further comprising one or more natural products selected from the group consisting of raw oats in hull, barley cereal, *Yucca* leaves, white onion, green lemon peel and rinds, and green leaves of citronella.

6. A biological agent for inhibiting pathogens in plant material susceptible to pathogen infection comprising the biopesticidal composition as set forth in claim 2.

* * * * *